(12) United States Patent
Murakami et al.

(10) Patent No.: US 10,487,307 B2
(45) Date of Patent: *Nov. 26, 2019

(54) CULTURE METHOD FOR PLURIPOTENT STEM CELLS

(71) Applicant: FUJIFILM CORPORATION, Minato-ku, Tokyo (JP)

(72) Inventors: Yuta Murakami, Kanagawa (JP); Sanae Nomiyama, Kanagawa (JP); Keita Hagiya, Kanagawa (JP); Yuichi Yoshino, Kanagawa (JP); Rie Hando, Kanagawa (JP); Yoshihide Iwaki, Kanagawa (JP); Tasuku Sasaki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 15/064,619

(22) Filed: Mar. 9, 2016

(65) Prior Publication Data

US 2016/0251613 A1 Sep. 1, 2016

Related U.S. Application Data

(63) Continuation of application No. PCT/JP2014/073947, filed on Sep. 10, 2014.

(30) Foreign Application Priority Data

Sep. 10, 2013 (JP) .................. 2013-187440

(51) Int. Cl.
C07K 14/78 (2006.01)
C12N 5/071 (2010.01)
C12N 5/00 (2006.01)
C12N 5/074 (2010.01)

(52) U.S. Cl.
CPC ......... *C12N 5/0068* (2013.01); *C12N 5/0696* (2013.01); *C12N 2500/25* (2013.01); *C12N 2500/32* (2013.01); *C12N 2500/38* (2013.01); *C12N 2500/90* (2013.01); *C12N 2501/119* (2013.01); *C12N 2501/15* (2013.01); *C12N 2533/30* (2013.01); *C12N 2533/50* (2013.01)

(58) Field of Classification Search
CPC .......................... C12N 5/0696; C12N 5/0068
See application file for complete search history.

(56) References Cited

U.S. PATENT DOCUMENTS

2010/0143442 A1* 6/2010 Upton .................. C07K 14/65
424/423

2012/0225480 A1 9/2012 Amit et al.
2012/0301962 A1* 11/2012 Thomson ............. C12N 5/0606
435/377
2015/0050737 A1 2/2015 Murakami et al.
2017/0022473 A1* 1/2017 Murakami ........... C12N 5/0696

FOREIGN PATENT DOCUMENTS

| JP | 2001-17183 A | 1/2001 | |
|---|---|---|---|
| JP | 2010029186 | * 1/2010 | ........... C12N 5/0068 |
| JP | 2010-29186 A | 2/2010 | |
| WO | WO-2004069871 A1 * | 8/2004 | ............. C07K 14/65 |
| WO | 2011/058558 A2 | 5/2011 | |
| WO | 2013/164970 A1 | 11/2013 | |
| WO | WO-2013164970 A1 * | 11/2013 | ........... C12N 5/0696 |

OTHER PUBLICATIONS

Prowse et al(Biomaterial, 8281-8288 (Year: 2010).*
Kyte Jet al J. Mol. Biol, 157: 105-132 (Year: 1982).*
Chen et al Nature Methods, 8, 5, 424-431 (Year: 2011).*
Ngo et al., The protein Folding Problem and Tertiary Structure Prediction, pp. 492-495 and (Year: 1994).*
Skolnick et al Trends in Biotech, 18, 34-39 (Year: 2000).*
Chunhui Xu et al., "Feeder-free growth of undifferentiated human embryonic stem cells," Nature Biotechnology, vol. 19, Issue No. 10, pp. 971-974, Oct. 2001, Nature Publishing Group (UK).
A.B.J. Prowse et al., "Long term culture of human embryonic stem cells on recombinant vitronectin in ascorbate free media," Biomaterials, vol. 31, Issue No. 32, pp. 8281-8288, 2010, Elsevier Ltd. (UK).
Z. Melkoumian et al., "Synthetic peptide-acrylate surfaces for long-term self-renewal and cardiomyocyte differentiation of human embryonic stem cells," Nature Biotechnology, vol. 28, Issue No. 6, pp. 606-610, Jun. 2010, Nature Publishing Group (UK).

(Continued)

*Primary Examiner* — Anoop K Singh
(74) *Attorney, Agent, or Firm* — Solaris Intellectual Property Group, PLLC

(57) ABSTRACT

A culture method for pluripotent stem cells includes culturing pluripotent stem cells on a cell culture surface of a support by using a medium in which the concentration of 2-mercaptoethano is equal to or less than 10 μM in the presence of a polypeptide consisting of 40 to 450 amino acid residues, in which the polypeptide includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQRFRHRNRKGYRSQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to the cell culture surface of the support, or (2-iii) an amino acid sequence which is formed by the addition, substitution, or deletion of 1 to 30 amino acids in the amino acid sequence represented by SEQ ID NO: 2 and exhibits adsorbability with respect to the cell culture surface of the support.

11 Claims, 9 Drawing Sheets

Specification includes a Sequence Listing.

(56) References Cited

OTHER PUBLICATIONS

G. Chen et al., "Chemically defined conditions for human iPSC derivastion and culture," Nature Methods, vol. 8, Issue No. 5, pp. 424-429, May 2011, Nature Publishing Group (UK).
The International Stem Cell Initiative Consortium, "Comparison of defined culture systems for feeder cell free propagation of human embryonic stem cells," In Vitro Cell. Dev. Biol.—Animal, vol. 46, Issue No. 3, pp. 247-258, Springer (US), Apr. 2010.
M. Furue et al., "Heparin promotes the growth of human embryonic stem cells in a defined serum-free medium," PNAS, vol. 105, Issue No. 36, pp. 13409-13414, Sep. 2008, United States National Academy of Sciences (US).
International Search Report issued in International Application No. PCT/JP2014/073947 dated Dec. 16, 2014.
Written Opinion of the ISA issued in International Application No. PCT/JP2014/073947 dated Dec. 16, 2014.
Japanese Office Action dated Aug. 23, 2016 in corresponding Japanese Patent Application No. 2015-536601 and a Partial English Translation thereof.

* cited by examiner

CULTURE METHOD FOR PLURIPOTENT STEM CELLS

CROSS-REFERENCE TO RELATED APPLICATIONS

This application is a continuation application of International Application No. PCT/JP2014/073947, filed Sep. 10, 2014, the disclosure of which is incorporated herein by reference in its entirety. Further, this application claims priority from Japanese Patent Application No. 2013-187440, filed Sep. 10, 2013, the disclosure of which is incorporated herein by reference in its entirety.

INCORPORATION OF SEQUENCE LISTING

The Sequence Listing associated with this application is provided in text format as a file entitled "SequenceListing2.TXT" created on May 19, 2016. The text file has a size of 54 kb and was filed via EFS-Web. The information in electronic format of the Sequence Listing is incorporated herein by reference in its entirety.

BACKGROUND OF THE INVENTION

1. Field of the Invention

The present invention relates to a culture method for pluripotent stem cells, a culture kit, and a medium for pluripotent stem cell culture.

2. Description of the Related Art

For the purpose of the recovery of functions of damaged tissues, various regenerative medical techniques are being developed. Among these, a large number of techniques relating to totipotent or pluripotent stem cells of primates, particularly, human beings that is ultimately aimed at the regeneration of tissues has been reported. Especially, induced pluripotent stem cells (iPS cells) have an advantage in that these cells lessen ethical issues because they are induced from somatic cells unlike embryonic stem cells.

In a case where the totipotent or pluripotent stem cells (both will be collectively simply referred to as "pluripotent stem cells" in the present invention) of primates are cultured, the cells need to be kept undifferentiated for a long period of time. For culturing the undifferentiated pluripotent stem cells for a long period of time, generally, feeder cells such as mouse fibroblasts are used.

However, it has been pointed out that the use of heterogeneous animal-derived feeder cells such as mouse fibroblasts leads to a likelihood that foreign substances such as heterogeneous animal-derived antigenic substances may be mixed into the culture solution. Therefore, in a case where the totipotent or pluripotent stem cells are used for medical purposes or for the purposes equivalent to medical purposes, the cells need to be cultured without feeder cells.

In consideration of the circumstances described above, cell-adhesive materials functioning as the feeder cells are being developed. For example, Nature Biotechnology, 2001, Vol. 19, pp. 971-974 discloses that human embryonic stem cells kept undifferentiated are successfully cultured by using a matrix gel which is a component extracted from mouse sarcoma as a substituent for feeder cells.

JP2001-17183A discloses a feeder cell-free cellular composition containing growing primordial cells of primates, and discloses, as a preferred embodiment, a cellular composition further containing an extracellular matrix. JP2010-29186A discloses a cell culture substrate in which a plasma-polymerized cell culture surface is additionally coated with a coating solution containing an extracellular matrix protein at a predetermined concentration and an aqueous solvent. JP2010-29186A describes that the cell culture substrate has excellent adhesiveness helpful to avoid the differentiation of embryonic stem cells.

Biomaterials, 2010, November; Vol. 31(32), pp. 8281-8288 and Nature Biotechnology, 2010, Vol. 28, No. 6, pp. 606-610 disclose a recombinant peptide or a synthetic peptide having a partial sequence of vitronectin that makes a contribution to long-term culture of embryonic stem cells. Specifically, the above documents disclose a sequence consisting of the $1^{st}$ to $52^{nd}$ amino acids of natural vitronectin (see Biomaterials, 2010, November; Vol. 31(32), pp. 8281-8288) and a sequence consisting of the $41^{st}$ to $52^{nd}$ amino acids of natural vitronectin including an RGD sequence (Nature Biotechnology, 2010, Vol. 28, No. 6, pp. 606-610) respectively. It is known that these peptides make it possible to avoid a likelihood of intermixing of antigenic substances because they are non-biological samples and can be excellently produced in an industrial manner. Specifically, Biomaterials, 2010, November; Vol. 31(32), pp. 8281-8288 and Nature Biotechnology, 2010, Vol. 28, No. 6, pp. 606-610 disclose an example in which embryonic stem cells are cultured for a long period of time by using a recombinant peptide or a synthetic peptide having a partial sequence of human vitronectin.

Generally, undifferentiated cells such as embryonic stem cells (ESC) tend to have a low growth ability. Therefore, in many cases, such cells are co-cultured with feeder cells. However, during the co-culture using the feeder cells, natural components derived from the feeder cells are mixed into the medium. Furthermore, because the undifferentiated cells tend to need to be cultured in a state of retaining pluripotency, the state of the cells and the components of the medium need to be strictly controlled.

In this respect, various serum-free media that exhibit high cell growth activity have been suggested, and specifically, Essential 8 (trade name, will not be mentioned hereinafter, see Nature Methods, 2011, Vol. 8, pp. 424-429) and the like have been known.

SUMMARY OF THE INVENTION

However, both the recombinant peptide and the synthetic peptide having a partial sequence of human vitronectin disclosed in JP2010-29186A and Nature Biotechnology, 2010, Vol. 28, No. 6, pp. 606-610 exhibit low adsorbability with respect to a culture vessel, and accordingly, a step of chemically bonding the peptides to the culture vessel is required. Therefore, the culture surface to which those peptides are bonded cannot be freely selected, and the versatility and simplicity deteriorate. Furthermore, it cannot be said that the polypeptides of the related art have sufficient cell culture performance of inducing the growth of pluripotent stem cells such as embryonic stem cells (ESC) and induced pluripotent stem cells (iPS) while keeping these cells undifferentiated.

In addition, the properties of the pluripotent stem cells are greatly different from those of matured cells or cell lines. Therefore, regarding the components of the medium of the pluripotent stem cells, further investigation is required.

Accordingly, objects of the present invention are to provide a culture method for pluripotent stem cells that makes it possible to keep the pluripotent stem cells undifferentiated and to induce high growth activity for the pluripotent stem cells and to provide a culture kit and a medium for pluripotent stem cell culture that are used for the method.

The present invention is as follows.

[1] A culture method for pluripotent stem cells including culturing pluripotent stem cells on a cell culture surface of a support in the presence of a polypeptide consisting of 40 to 450 amino acid residues by using a medium in which the concentration of 2-mercaptoethanol is equal to or less than 10 µM, in which the polypeptide includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQRFRHRNRKGYRSQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to the cell culture surface of the support, or (2-iii) an amino acid sequence which is formed by the addition, substitution, or deletion of 1 to 30 amino acid residues in the amino acid sequence represented by SEQ ID NO: 2 and exhibits adsorbability with respect to the cell culture surface of the support.

[2] The culture method for pluripotent stem cells described in [1], in which the medium does not contain 2-mercaptoethanol.

[3] The culture method for pluripotent stem cells described in [1] or [2], in which the medium contains water, a salt, an amino acid, vitamin, selenium, a carbon source, FGF, TGF-β, insulin, and transferrin.

[4] The culture method for pluripotent stem cells described in any one of [1] to [3], in which the medium is a serum-free medium.

[5] The culture method for pluripotent stem cells described in any one of [1] to [4], in which a GRAVY value of the polypeptide is −2.0 to −0.95.

[6] The culture method for pluripotent stem cells described in any one of [1] to [5], in which the polypeptide further includes a third domain including one of the following amino acid sequences (3-i) to (3-iii): (3-i) an amino acid sequence, which consists of the $56^{th}$ to $341^{st}$ amino acid residues in an amino acid sequence represented by SEQ ID NO: 3, or a partial amino acid sequence thereof, (3-ii) an amino acid sequence which shares sequence identity of equal to or higher than 50% with the amino acid sequence (3-ii) or a partial amino acid sequence thereof, and (3-iii) an amino acid sequence which is formed by the addition, substitution, or deletion of 1 to 30 amino acid residues in the amino acid sequence (3-i) or a partial amino acid sequence thereof.

[7] The culture method for pluripotent stem cells described in any one of [1] to [6], in which the polypeptide further includes a fourth domain including one of the following amino acid sequences (4-i) to (4-iii): (4-i) an amino acid sequence, which consists of the $374^{th}$ to $459^{th}$ amino acid residues in the amino acid sequence represented by SEQ ID NO: 3, or a partial amino acid sequence thereof, (4-ii) an amino acid sequence which shares sequence identity of equal to or higher than 50% with the amino acid sequence (4-i) or a partial amino acid sequence thereof, and (4-iii) an amino acid sequence which is formed by the addition, substitution, or deletion of 1 to 30 amino acid residues in the amino acid sequence (4-i) or a partial amino acid sequence thereof

[8] The culture method for pluripotent stem cells described in any one of [1] to [7], in which the polypeptide is at least one kind of polypeptide selected from the group consisting of (a) a polypeptide which has an amino acid sequence represented by one of SEQ ID NO: 4 to SEQ ID NO: 25, (b) a polypeptide which has an amino acid sequence formed by the deletion, substitution, or addition of one amino acid residue or several amino acid residues in the amino acid sequence represented by one of SEQ ID NO: 4 to SEQ ID NO: 25 and exhibits adsorbability with respect to the cell culture surface of the support, and (c) a polypeptide which has an amino acid sequence sharing sequence identity of equal to or higher than 80% with the amino acid sequence represented by one of SEQ ID NO: 4 to SEQ ID NO: 25 and exhibits adsorbability with respect to the cell culture surface of the support.

[9] The culture method for pluripotent stem cells described in any one of [1] to [8], in which the polypeptide is a polypeptide which has an amino acid sequence sharing sequence identity of equal to or higher than 90% with the amino acid sequence represented by one of SEQ ID NO: 4 to SEQ ID NO: 25 and can be adsorbed onto the cell culture surface of the support.

[10] The culture method for pluripotent stem cells described in any one of [1] to [9], in which the polypeptide is a polypeptide which has an amino acid sequence sharing sequence identity of equal to or higher than 95% with the amino acid sequence represented by one of SEQ ID NO: 4 to SEQ ID NO: 25 and exhibits adsorbability with respect to the cell culture surface of the support.

[11] The culture method for pluripotent stem cells described in any one of [1] to [10], in which the support is made of polystyrene having a plasma-treated cell culture surface.

[12] The culture method for pluripotent stem cells described in any one of [1] to [11], in which the pluripotent stem cells are at least one kind of cells selected from the group consisting of embryonic stem cells, induced pluripotent stem cells, somatic stem cells, cells from inner cell mass of fertilized eggs, and early embryonic cells.

[13] The culture method for pluripotent stem cells described in any one of [1] to [12], in which the pluripotent stem cells are induced pluripotent stem cells.

[14] The culture method for pluripotent stem cells described in any one of [1] to [13], in which the amount of the polypeptide applied to the cell culture surface is 1 pmol/cm$^2$ to 1,000 pmol/cm$^2$.

[15] The culture method for pluripotent stem cells described in any one of [1] to [14], further including obtaining a polypeptide-coated cell culture surface of the support by applying a polypeptide consisting of 40 to 450 amino acid residues to the cell culture surface of the support, in which the polypeptide includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQR- FRHRNRKGYRSQRGHSRGRNQN (SEQ ID NO: 2), (2-ii) an amino acid sequence which shares sequence identity of equal to or higher than 50% with the amino acid sequence represented by SEQ ID NO: 2 and can be adsorbed onto the cell culture surface of the support, or (2-iii) an amino acid sequence which is formed by the addition, substitution, or deletion of 1 to 30 amino acid residues in the amino acid sequence represented by SEQ ID NO: 2 and exhibits adsorbability with respect to the cell culture surface of the support.

[16] A culture kit for pluripotent stem cells including a polypeptide consisting of 40 to 450 amino acid residues and a medium in which the concentration of 2-mercaptoethanol is equal to or less than 10 µM, in which the polypeptide includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQRFRHRNRKGYRSQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to the cell culture surface of the support, or (2-ii) an amino acid sequence which is formed by the addition, substitution, or deletion of 1 to 30 amino acid residues in the amino acid sequence represented by SEQ ID NO: 2 and exhibits adsorbability with respect to the cell culture surface of the support.

[17] A medium for pluripotent stem cell culture in which the concentration of 2-mercaptoethanol is equal to or less than 10 µM.

According to the present invention, it is possible to provide a culture method for pluripotent stem cells that makes it possible to keep the pluripotent stem cells undifferentiated and induce high growth activity for the pluripotent stem cells and to provide a culture kit and a medium for pluripotent stem cell culture that are used for the method.

DESCRIPTION OF THE PREFERRED EMBODIMENTS

Figure 1:
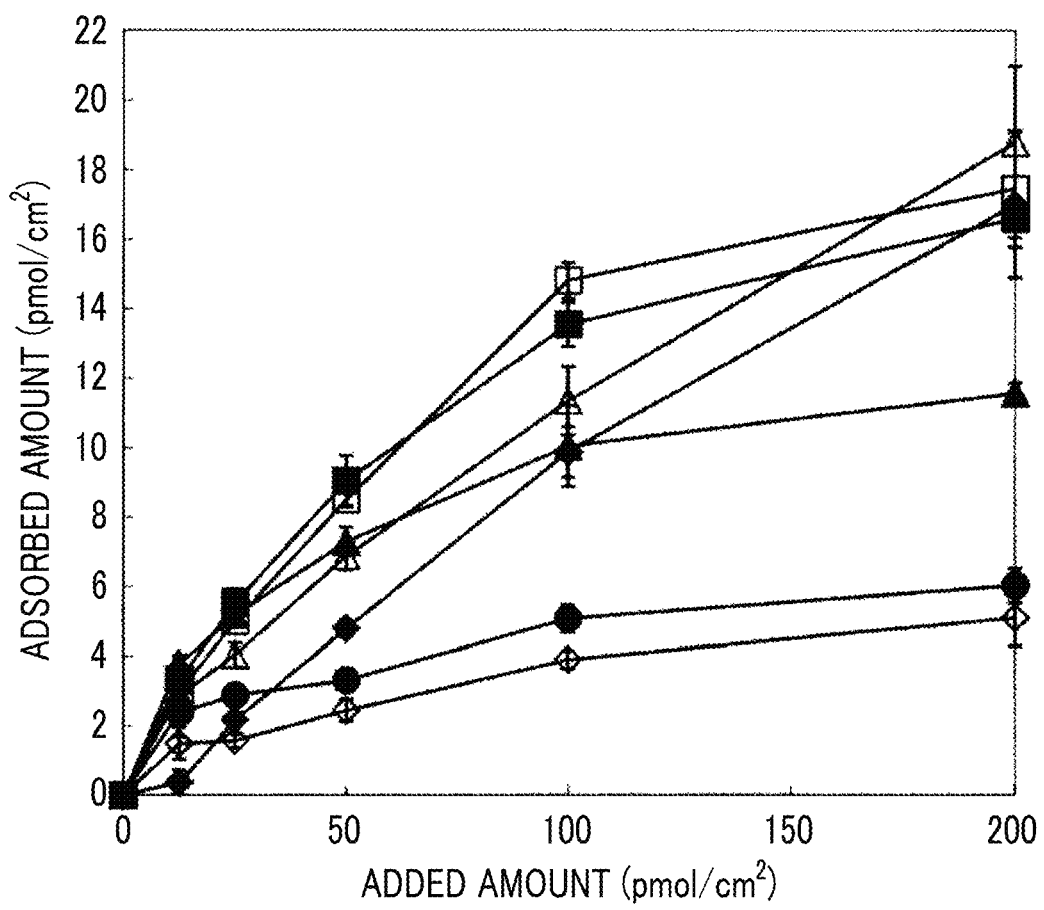
FIG. 1 is a graph showing the results of a test performed to check how well each polypeptide in the reference examples of the present invention is adsorbed onto the surface of a culture plate.

The culture method for pluripotent stem cells of the present invention is a culture method for pluripotent stem cells including culturing pluripotent stem cells on a cell culture surface of a support in the presence of a polypeptide consisting of 40 to 450 amino acid residues by using a medium in which the concentration of 2-mercaptoethanol is equal to or less than 10 µM, in which the polypeptide includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQRFRHRNRKGYR-SQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to the cell culture surface of the support, or (2-iii) an amino acid sequence which is formed by the addition, substitution, or deletion of 1 to 30 amino acid residues in the amino acid sequence represented by SEQ ID NO: 2 and exhibits adsorbability with respect to the cell culture surface of the support.

In order to develop a recombinant protein that enables pluripotent stem cells to grow in an undifferentiated state, the inventors of the present invention repeated intensive research. As a result, they obtained knowledge that a predetermined polypeptide, which includes a predetermined N-terminal partial sequence of human vitronectin and consists of amino acid residues that exhibit adsorbability with respect to a cell culture surface of a support, enables pluripotent stem cells to grow in a culture solution not containing a heterogeneous animal-derived component for a long period of time while maintaining an undifferentiated state. Furthermore, the inventors of the present invention obtained knowledge that if a medium in which the concentration of 2-mercaptoethanol is equal to or less than 10 µM is used at the time of growing pluripotent stem cells on a cell culture surface of a support by using the aforementioned predetermined polypeptide, the pluripotent stem cells can be kept undifferentiated and high growth activity can be induced for the pluripotent stem cells. The present invention is based on the above knowledge.

According to the present invention, pluripotent stem cells are cultured on a cell culture surface of a support in the presence of a predetermined polypeptide by using a medium in which the concentration of 2-mercaptoethanol is equal to or less than 10 Therefore, according to the present invention, it is possible to provide a culture method for pluripotent stem cells that can keep the pluripotent stem cells undifferentiated and can induce high growth activity for the pluripotent stem cells.

Hereinafter, the present invention will be described.

The polypeptide according to the present invention includes (1) a first domain including at least one amino acid sequence selected from the group consisting of an amino acid sequence represented by CSYYQSC (SEQ ID NO: 1) and an amino acid sequence represented by RGD and (2) a second domain including (2-i) an amino acid sequence which is represented by PRPSLAKKQRFRHRNRKGYR-SQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to the cell culture surface of the support, or (2-iii) an amino acid sequence which is formed by the addition, substitution, or deletion of 1 to 30 amino acid residues in the amino acid sequence represented by SEQ ID NO: 2 and exhibits adsorbability with respect to the cell culture surface of the support, and consists of 40 to 450 amino acid residues. In the present specification, such a polypeptide is referred to as a "polypeptide for culture" in some cases.

In the present specification, the term "step" includes not only an independent step, but also a step that cannot be clearly distinguished from other steps as long as the intended object thereof is achieved.

In the present specification, a range of numerical values represented by using "to" means a range which includes numerical values listed before and after "to" as a minimum value and a maximum value respectively.

In the present specification, in a case where there is a plurality of substances corresponding to each component in a composition, unless otherwise specified, the amount of each component in the composition means the total amount of the plurality of substances present in the composition.

In the present specification, "homogeneous" means a human being, and "heterogeneous" means an animal other than a human being. As long as a component or substance used in the present invention is a component or substance derived from an animal that belongs to the primates, the component or substance can be preferably used in the present invention as a component or substance derived from a homogeneous animal.

In the present specification, an amino acid residue in an amino acid sequence is designated by one letter (for example, "G" for a glycine residue) or by three letters (for example, "Gly" for a glycine residue) in some cases as widely known in the field of the related art.

In the present invention, unless otherwise specified, "%" relating to an amino acid sequence of a polypeptide is based on the number of amino acid (or imino acid) residues.

In the present specification, the expression such as "the corresponding amino acid residue" used for a specific amino acid residue in an amino acid sequence means an amino acid residue in an amino acid sequence that is in the same position as a specific amino acid residue in another amino acid sequence as a standard in a case where sequence alignment are performed on two or more contrasting amino acid sequences by a method known in the field of the related art in consideration of insertion, deletion, and substitution so as to maximize the number of amino acid residues identical to each other.

In the present specification, "sequence identity" relating to an amino acid sequence can refer to a value calculated by using a BLAST package (see Ausubel et al., 1999 Short Protocols in Molecular Biology, 4th Ed—Chapter 18). For example, to share sequence identity of equal to or higher than 50% with SEQ ID NO: 2 means that a value of Max. Identities in BLAST is equal to or greater than 50.

In the present invention, vitronectin means human vitronectin. Specifically, the vitronectin is the full-length polypeptide constituted with 495 amino acid residues represented by SEQ ID NO: 3. It has been confirmed that natural vitronectin is a sugar protein having a sugar chain in a portion of the sequence thereof.

```
SEQ ID NO: 3:
DQESCKGRCTEGFNVDKKCQCDELCSYYQSCCTDYTAECKPQVTRG

DVFTMPEDEYTVYDDGEEKNNATVHEQVGGPSLTSDLQAQSKGNPE

QTPVLKPEEEAPAPEVGASKPEGIDSRPETLHPGRPQPPAEEELCS

GKPFDAFTDLKNGSLFAFRGQYCYELDEKAVRPGYPKLIRDVWGIE

GPIDAAFTRINCQGKTYLFKGSQYWRFEDGVLDPDYPRNISDGFDG

IPDNVDAALALPAHSYSGRERVYFFKGKQYWEYQFQHQPSQEECEG

SSLSAVFEHFAMMQRDSWEDIFELLFWGRTSAGTRQPQFISRDWHG

VPGQVDAAMAGRIYISGMAPRPSLAKKQRFRHRNRKGYRSQRGHSR

GRNQNSRRPSRATWLSLFSSEESNLGANNYDDYRMDWLVPATCEPI

QSVEFFSGDKYYRVNLRTRRVDTVDPPYPRSIAQYWLGCPAPGHL
```

The culture method of the present invention includes culturing pluripotent stem cells (hereinafter, referred to as a culture step) on a cell culture surface of a support in the presence of the polypeptide for culture by using a medium in which the concentration of 2-mercaptoethanol is equal to or less than 10 If necessary, the culture method of the present invention may include other steps.

<Pluripotent Stem Cells>

The pluripotent stem cells to be cultured are pluripotent stem cells of an animal that belongs to primates. Specifically, the pluripotent stem cells include embryonic stem cells (ES cells), induced pluripotent stem cells (iPS cells), somatic stem cells, cells from inner cell mass of fertilized eggs, early embryonic cells, and the like. As the pluripotent stem cells, one kind of these cells may be used singly, or if necessary, two or more kinds thereof may be used by being mixed together. The iPS cells include the cells described in Nature, 2007, Jul. 19; Vol. 448, pp. 313-317; Cell, 2006, Aug. 25; Vol. 126(4), pp. 663-676 and cells similar to the above cells.

Examples of the pluripotent stem cells preferably used in the present invention include iPS cells. The pluripotent stem cells preferably used in the present invention are particularly preferably iPS cells.

Examples of the animal that belongs to primates include a human being, a monkey, a gorilla, and the like. The animal that belongs to primates is preferably a human being congeneric with the polypeptide for culture.

<Support>

In the culture step, the pluripotent stem cells are cultured on a cell culture surface of a support.

In order to culture the pluripotent stem cells on the cell culture surface of the support, the pluripotent stem cells should be seeded onto the cell culture surface of the support.

The support used for culture has a surface used for cell culture, that is, a cell culture surface. The cell culture surface means a surface to which cells can adhere when the cells are seeded onto the surface for growth.

As the support, those known as a support for cell culture in the related art can be used as they are. Examples of the support may include plastic (for example, polystyrene, an acrylonitrile-butadiene-styrene resin, a polycarbonate resin, and a polyester resin), glass, filter with fine pores (for example, cellulose, nylon, glass fiber, polyester, and polycarbonate), a material for a bioreactor (may include hollow fiber tubes or microcarrier beads) used in batch cell culture, continuous cell culture, or genetic engineering (for example, a bioreactor), polyethylene terephthalate, Teflon (registered trademark), ceramic and polymer materials relating thereto, and the like.

The support is preferably a support having a plasma-treated cell culture surface obtained by coating a cell culture surface with a plasma-polymerized thin film. In view of hydrophobicity of the cell culture surface, the support is more preferably a support made of polystyrene having a plasma-treated cell culture surface.

The shape of the support is not particularly limited, and the support may have any shape as long as it is applicable to the culture of pluripotent stem cells. Examples of vessels with such a shape include a multi-well plate (for example, a 6-well plate, a 12-well plate, a 24-well plate, and a 96-well plate), a culture dish (for example, a petri dish), a tube, a culture flask, a roller bottle, a flask for shake culture, and the like.

<Polypeptide for Culture>

In the culture step, the pluripotent stem cells are cultured in the presence of the polypeptide for culture.

The polypeptide for culture is a polypeptide which includes the following first and second domains and consists of 40 to 450 amino acid residues.

(1) A first domain including at least one amino acid sequence selected from the group consisting of an amino acid sequence represented by CSYYQSC (SEQ ID NO: 1) and an amino acid sequence represented by RGD (hereinafter, simply referred to as an RGD sequence), (2) A second domain including (2-i) an amino acid sequence which is represented by PRPSLAKKQRFRHRN-RKGYRSQRGHSRGRNQN (SEQ ID NO: 2), (2-ii) an amino acid sequence which shares sequence identity of equal to or higher than 50% with the amino acid sequence represented by SEQ ID NO: 2 and exhibits adsorbability with respect to a culture vessel, or (2-iii) an amino acid sequence which is formed by the addition, substitution, or deletion of 1 to 30 amino acid residues in the amino acid sequence represented by SEQ ID NO: 2 and exhibits adsorbability with respect to a culture vessel.

In the polypeptide for culture, the first domain including a predetermined amino acid sequence has excellent cell adhesiveness. Therefore, the polypeptide enables the pluripotent stem cells to excellently grow for a long period of time while maintaining the undifferentiated state.

Furthermore, the second domain including a predetermined sequence makes a contribution to the adsorbability of the polypeptide with respect to the cell culture surface of the support. Therefore, it is not necessary to perform a treatment for fixing the polypeptide onto the culture surface by chemical bonding. In addition, because both the first and second domains are included in the polypeptide, the pluripotent stem cells tend not to be easily exfoliated from the cell culture surface of the support for the duration of culture. As a result, the pluripotent stem cells can grow for a long period of time while maintaining the undifferentiated state, and the handleability in the culture operation can be improved.

Unlike the natural human vitronectin, the polypeptide for culture can eliminate a risk of intermixing of an antigenic substance or an infection source. In addition, the polypeptide for culture can retain the performances equivalent to those of the natural vitronectin, that is, the adhesiveness with respect to the pluripotent stem cells, the cell growth properties, and the properties of maintaining the undifferentiated state.

The pluripotent stem cells cultured in the presence of the polypeptide for culture (preferably in the absence of a heterogeneous animal-derived component or the like) can completely eliminate or significantly reduce a likelihood that a foreign substance such as an antigenic substance derived from a sample or the like may be mixed into the cells. Therefore, in a case where the pluripotent stem cells cultured by the aforementioned culture method are used for medical purposes or for purposes equivalent to medical purposes, sufficient safety can be ensured.

The first domain includes at least one amino acid sequence selected from the group consisting of an amino acid sequence represented by SEQ ID NO: 1 and an RGD sequence.

The amino acid sequence represented by SEQ ID NO: 1 corresponds to seven amino acid residues consisting of the $25^{th}$ to $31^4$ amino acids residues in the amino acid sequence of vitronectin. Furthermore, the RGD sequence is a cell adhesive motif which corresponds to three amino acid residues consisting of the $45^{th}$ to $47^{th}$ amino acid residues in the amino acid sequence of vitronectin. All of these amino acid sequences are sequences positioned relatively on the N-terminal side of natural vitronectin. Presumably, these amino acid sequences may exhibit adhesiveness with respect to the undifferentiated pluripotent stem cells and thus enable the pluripotent stem cells kept undifferentiated to grow. Theoretically, it is considered that for this reason, a polypeptide containing none of these amino acid sequences has poor cell adhesiveness and does not enable the pluripotent stem cells kept undifferentiated to grow. However, the present invention is not limited to this theory.

Two cysteine residues in the amino acid sequence represented by SEQ ID NO: 1 may be cross-linked with each other. In this way, a high-order structure is formed in the amino acid sequence represented by SEQ ID NO: 1, and the adhesiveness with respect to the pluripotent stem cells tend to be improved.

Here, "enabling the pluripotent stem cells to grow in an undifferentiated state" means that the pluripotent stem cells retains differentiation potency for the duration of culture. Whether or not the pluripotent stem cells are in an undifferentiated state can be evaluated by a known method. For example, it can be evaluated by the methods known to those in the related art, such as expression of molecular markers (measuring the expression of SSEA-4 and/or Oct-4 by means of flow cytometry, immunostaining by using Oct-4 and/or NANOG, and the like), checking the pluripotent differentiation by in-vitro experiment, and checking the formation of teratoma resulting from the transplantation of the cells into an immunodeficient mouse. Whether or not the pluripotent stem cells are growing should be checked through a common method by means of visual observation using various microscopes, by means of a technique using a test for reactivity such as ALP activity, flow cytometery, or the like, or by means of other techniques. In the present invention, the duration for which the pluripotent stem cells are cultured in a state of retaining the differentiation potency can be set to be, for example, one month, although the duration varies with the culture conditions and the state of the pluripotent stem cells.

The first domain in the polypeptide for culture should include any one of the amino acid sequences selected from the group consisting of the amino acid sequence represented by SEQ ID NO: 1 and the RGD sequence. From the viewpoint of the cell adhesiveness and the cell growth properties, the first domain in the polypeptide for culture preferably includes both the amino acid sequence represented by SEQ ID NO: 1 and the RGD sequence.

The first domain may have an amino acid sequence other than the amino acid sequence represented by SEQ ID NO: 1 and the RGD sequence. From the viewpoint of the cell adhesiveness and the cell growth properties of the first domain, examples of such an amino acid sequence include (1a) and amino acid sequence consisting of the $1^{st}$ to $24^{th}$ amino acid residues of the amino acid sequence of human vitronectin represented by SEQ ID NO: 3, (1b) an amino acid sequence consisting of the $48^{th}$ to $55^{th}$ amino acid residues in the amino acid sequence of human vitronectin represented by SEQ ID NO: 3, (1c) an amino acid sequence consisting of the $32^{nd}$ to $44^{th}$ amino acid residues in the amino acid sequence of human vitronectin represented by SEQ ID NO: 3, and a combination of these. Each of the amino acid sequences (1a) to (1c) may have a sequence in which 1 to 30 amino acid residues are substituted, deleted, or omitted, within a range that does not impair the cell adhesiveness and the cell growth properties of the first domain. Furthermore, each of the amino acid sequences (1a) to (1c) may have an amino acid sequence which shares sequence identity of equal to or higher than 50% with each of the amino acid sequences (1a) to (1c).

The first domain can include at least one amino acid sequence selected from the group consisting of the amino acid sequences (1a) to (1c), in addition to the amino acid sequence represented by SEQ ID NO: 1 and the RGD sequence. From the viewpoint of the cell adhesiveness and the cell growth properties, it is preferable that the first domain includes both the amino acid sequence represented by SEQ ID NO: 1 and the RGD sequence and further includes an amino acid sequence which consists of the $1^{st}$ to $55^{th}$ amino acid residues of the amino acid sequence represented by SEQ ID NO: 3, an amino acid sequence similar to this amino acid sequence, or a partial amino acid sequence thereof.

From the viewpoint of the cell adhesiveness and the growth properties, the first domain can consist of 3 to 60 amino acid residues and preferably can consist of 10 to 55 amino acid residues.

The second domain includes the amino acid sequence consisting of 32 amino acid residues represented by SEQ ID NO: 2. From the viewpoint of ease of purifying the polypeptide for culture, the second domain includes the amino acid sequence represented by SEQ ID NO: 2. The amino acid sequence represented by SEQ ID NO: 2 is included in a portion of a hemopexin-like domain II positioned on the C-terminal side of the natural vitronectin and corresponds to a heparin binding domain consitituted with the $342^{nd}$ to $373^{rd}$ amino acid residues of the amino acid sequence represented by SEQ ID NO: 3. Hereinafter, the amino acid sequence represented by SEQ ID NO: 2 will be referred to a heparin binding domain in some cases.

Presumably, the polypeptide for culture may exhibit adsorbability with respect to the cell culture surface of the support because the polypeptide has the heparin binding domain. Theoretically, it is considered that for this reason, the polypeptide for culture enables the pluripotent stem cells to grow for a long period of maintaining the undifferentiated state. However, the present invention is not limited to the theory.

Furthermore, because the polypeptide for culture includes the heparin binding domain, the hydrophilicity of the polypeptide for culture is ensured, and the hydrophobic aggregation of the polypeptide tends to be inhibited. As a result, it is easy to purify the polypeptide for culture, and the production efficiency can be improved.

Herein, "exhibiting adsorbability with respect to the cell culture surface of the support" means that the polypeptide for culture can be physically adsorbed onto the cell culture surface of a target support (hereinafter, simply referred to as a "culture surface" in some cases) without chemically reacting with the culture surface. Whether or not the polypeptide exhibits adsorbability with respect to the culture surface of the support can be evaluated by the following method, for example. In the method, a solution containing the polypeptide is added in an amount of 200 pmol/cm$^2$ to a plasma-treated culture surface of a polystyrene support, and the support is left to stand for 2 hours at 37° C. and then washed twice with a phosphate buffer solution. Thereafter, whether or not the amount of the polypeptide remaining on the cell culture surface of the support is equal to or greater than 10 pmol/cm$^2$ is checked to evaluate the adsorbability of the polypeptide.

The amount of the polypeptide remaining on the cell culture surface can be measured by an Enzyme-Linked Immunosorbent Assay (ELISA) method in which the amount of the polypeptide binding to antibodies recognizing the polypeptide is determined or by a method in which the adsorbed polypeptide is hydrolyzed and the amount of the generated amino acid is determined by HPLC or the like.

The heparin binding domain may share sequence identity of equal to or higher than 50% (that is, 50% to 100%) with the amino acid sequence represented by SEQ ID NO: 2. The sequence identity may be preferably equal to or higher than 80% (that is, 80% to 100%), more preferably equal to or higher than 90% (that is, 90% to 100%), and even more preferably equal to or higher than 95% (that is, 95% to 100%). Furthermore, the heparin binding domain may be an amino acid sequence which enables the pluripotent stem cells to grow in an undifferentiated state and exhibits adsorbability with respect to the cell culture surface of the support.

The heparin binding domain may include an amino acid sequence formed by the deletion, substitution, or addition of 1 to 30 amino acids, preferably 1 to 15 amino acids, and more preferably 1 to 6 amino acids in the amino acid sequence represented by SEQ ID NO: 2. Furthermore, the heparin binding domain may be an amino acid sequence which exhibits adsorbability with respect to the cell culture surface of the support.

The polypeptide for culture should include the first and second domains, and the relative position thereof is not particularly limited. In the polypeptide for culture, the first domain is preferably positioned on the N-terminal side of the second domain.

The polypeptide for culture consists of 40 to 450 amino acid residues. If the number of the amino acid residues is less than 40, the cell adhesiveness, the cell growth properties, or the adsorbability with respect to the cell culture surface of the support cannot be sufficient. In contrast, if the number of the amino acid residues is greater than 450, the cell adhesiveness, the cell growth properties, and the adsorbability with respect to the cell culture surface of the support are not sufficiently demonstrated in some cases, and the protein molecules can be easily agglomerated, cross-linked, or aggregated. From the viewpoint of making it difficult for the protein molecules to be aggregated, the number of amino acid residues constituting the polypeptide for culture is preferably equal to or greater than 80, more preferably equal to or greater than 90, and even more preferably equal to or greater than 100. Furthermore, the number of amino acid residues constituting the polypeptide for culture is preferably equal to or less than 400, more preferably equal to or less than 250, even more preferably equal to or less than 170, and still more preferably equal to or less than 150. Any of the aforementioned upper limits may be combined with any of the aforementioned lower limits. For example, the polypeptide for culture preferably consists of 40 to 400 amino acid residues, more preferably consists of 80 to 250 amino acid residues, even more preferably consists of 80 to 150 amino acid residues, and still more preferably consists of 100 to 150 amino acid residues.

From the viewpoint of preventing the hydrophobic aggregation, it is preferable that the polypeptide for culture has a GRAVY value of −2.0 to −0.95. The GRAVY value (Kyte J., Doolittle R. F. (1982), J. Mol. Biol, 157: 105-132) represents the total average of a degree of hydrophobicity of the polypeptide. The greater the GRAVY value, the higher the degree of hydrophobicity. If the GRAVY value is equal to or less than −0.95, the occurrence of the hydrophobic aggregation tends to be easily inhibited. In contrast, if the GRAVY value is equal to or greater than −2.0, the polypeptide tend to be easily adsorbed onto the cell culture surface of the support, the undifferentiated cells tend to grow easily, and the adsorbability and the cell growth properties tend to be improved as the GRAVY value increases. In view of accomplishing both the inhibition of the aggregation and the adsorbability or the cell growth properties, the GRAVY value of the polypeptide is more preferably −1.70 to −0.975, and even more preferably −1.60 to −1.10. The smaller the number of the amino acid residues, the more the aggregation tends to occur. Therefore, in a case of a polypeptide consisting of 80 to 170 amino acid residues, in view of accomplishing both the inhibition of the aggregation and the adsorbability or the cell growth properties, the GRAVY value is preferably −1.70 to −0.975 and more preferably −1.60 to −1.10.

The GRAVY value can be adjusted by increasing or decreasing the proportion of a hydrophobic amino acid (for example, Trp, Tyr, Phe, Leu, Ile, Val, or Met) in the sequence or by increasing or decreasing the number of amino acid residues in the sequence.

It is preferable that the polypeptide for culture has an amino acid sequence other than the first and second domains. From the viewpoint of sufficiently exhibiting the cell adhesiveness and the adsorbability with respect to the cell culture surface of the support, the polypeptide for culture preferably includes the polypeptide represented by SEQ ID NO: 3, that is, a partial sequence of the amino acid sequence of human vitronectin. In this way, the polypeptide for culture can obtain properties close to the properties of the human vitronectin, for example, excellent adhesiveness and growth properties for the pluripotent stem cells.

From the viewpoint of the cell adhesiveness and the cell growth properties of the polypeptide for culture, the adsorbability with respect to the cell culture surface of the support, or the inhibition of aggregation, the partial amino acid sequence of the human vitronectin that can be include in the polypeptide for culture preferably includes at least one domain selected from the group consisting of the following third and fourth domains.

(3) A third domain having an amino acid sequence selected from an amino acid sequence, which consists of the 56$^{th}$ to 341$^{st}$ amino acid residues in the amino acid sequence represented by SEQ ID NO: 3, and a partial amino acid sequence thereof.

(4) A fourth domain having an amino acid sequence selected from an amino acid sequence, which consists of the 374$^{th}$ to 459$^{th}$ amino acid residues in the amino acid sequence represented by SEQ ID NO: 3, and a partial amino acid sequence thereof.

As the third domain, it is possible to select (3a) an amino acid sequence, which consists of the 132$^{nd}$ to 341$^{st}$ amino acid residues in the amino acid sequence represented by SEQ ID NO: 3, or a partial amino acid sequence thereof, (3b) an amino acid sequence, which consists of the 269$^{th}$ to 341$^{st}$ amino acid residues in the amino acid sequence represented by SEQ ID NO: 3, or a partial amino acid sequence thereof, (3c) an amino acid sequence, which consists of the 274$^{th}$ to 341$^{st}$ amino acid residues in the amino acid sequence represented by SEQ ID NO: 3, or a partial amino acid sequence thereof, or (3d) an amino acid sequence, which consists of the 294$^{th}$ to 341$^{st}$ amino acid residues in the amino acid sequence represented by SEQ ID NO: 3, or a partial amino acid sequence thereof, because the above amino acid sequences tend to inhibit the hydrophobic aggregation at the time of preparing the polypeptide. With the amino acid sequences (3a) to (3d), the hydrophobic aggregation tends to be able to be mitigated by the reducing the number of amino acid residues. It is particularly preferable to select the amino acid sequence (3d) because the hydrophobic aggregation tends to be able to be more reliably inhibited.

From the viewpoint of the adsorbability with respect to the cell culture surface of the support, as the fourth domain, it is possible to select an amino acid sequence, which consists of the 374$^{th}$ to 459$^{th}$ amino acid residues in the amino acid sequence represented by SEQ ID NO: 3, or a partial amino acid sequence thereof, an amino acid sequence, which consists of the 374$^{th}$ to 409$^{th}$ amino acid residues in the amino acid sequence represented by SEQ ID NO: 3, or a partial amino acid sequence thereof, or an amino acid sequence, which consists of the 374$^{th}$ to 379$^{th}$ amino acid residues in the amino acid sequence represented by SEQ ID NO: 3, or a partial amino acid sequence thereof.

Because the adsorbability with respect to the cell culture surface of the support is obtained, and the hydrophobic aggregation is easily inhibited at the time of preparing the polypeptide, the 374$^{th}$ to 379$^{th}$ amino acid residues are particularly preferable. By reducing the number of amino acids selected, the hydrophobic aggregation tends to be mitigated.

The partial amino acid sequence of the amino acid sequence constituting the third and fourth domains means an amino acid sequence constituted with three or more consecutive amino acid residues among a predetermined range of amino acid residues. The number of amino acid residues of the partial amino acid sequence should be selected within a range that does not exceed the aforementioned total number of amino acid residues of the polypeptide for culture.

The amino acid sequences constituting the third and fourth domains and partial amino acid sequences thereof may be amino acid sequences or partial amino acid sequences thereof which share sequence identity of equal to or higher than 50% (that is, 50% to 100%) with each of the amino acid sequences and the partial amino acid sequences thereof. The sequence identity may be preferably equal to or higher than 80% (that is, 80% to 100%), more preferably equal to or higher than 90% (that is, 90% to 100%), and even more preferably equal to or higher than 95% (that is, 95% to 100%). These amino acid sequences can be selected within a range that does not impair the cell adhesiveness of the polypeptide for culture and the adsorbability with respect to the cell culture surface of the support.

The amino acid sequences and the partial amino acid sequences thereof constituting the third and fourth domains may be amino acid sequences formed by the deletion, substitution, or addition of 1 to 30 amino acid residues, preferably 1 to 15 amino acid residues, and more preferably 1 to 5 amino acid residues in each of the amino acid sequences and the partial sequences thereof. These amino acid sequences formed by the deletion or the like of the amino acid residues can be selected within a range that does not impair the cell adhesiveness of the polypeptide for culture and the adsorbability with respect to the cell culture surface of the support.

By including the third domain, the polypeptide for culture tends to obtain an advantage of improving the adsorbability thereof with respect to the cell culture surface of the support. Furthermore, by including the fourth domain, the polypeptide for culture tends to obtain an advantage of further improving the adsorbability thereof with respect to the cell culture surface of the support. The polypeptide for culture may have one of the third and fourth domains.

The GRAVY value of the polypeptide for culture is preferably adjusted by increasing or decreasing the number of amino acid residues in the amino acid sequences constituting the third and fourth domains or by the substitution, deletion, addition, or the like of the amino acid residues, and particularly preferably adjusted by adjusting the length of the amino acid sequence constituting the third domain, because then the GRAVY value can be easily adjusted.

Among the amino acid residues constituting the amino acid sequence represented by SEQ ID NO: 3, the 56$^{th}$ to 131$^{st}$ amino acid residues, the 56$^{th}$ to 268$^{th}$ amino acid residues, the 269$^{th}$ to 273$^{rd}$ amino acid residue, or the 50$^{th}$ to 293$^{rd}$ amino acid residues may not be included in the polypeptide for culture. Presumably, an amino acid sequence consisting of the above amino acid residues may not make a contribution to the performance of the polypeptide for culture with respect to the pluripotent stem cells. Therefore, a sequence suitable for the adsorption of the polypeptide onto the cell culture surface of the support is selected.

In a case where the third domain includes an amino acid residue corresponding to a cysteine residue of the sequence represented by SEQ ID NO: 3, the third domain may have an amino acid residue other than the cysteine residue in the position of the cysteine residue. It is preferable that the third domain has an amino acid residue other than the cysteine residue because then intramolecular cross-linking or intermolecular cross-linking caused by the cysteine residue can be prevented. The amino acid residue substituting the cysteine residue is not particularly limited, and examples thereof include a serine residue, an alanine residue, a glycine residue, and the like. Among these, a serine residue and an alanine residue are preferable because these have a structure similar to that of cysteine.

The polypeptide for culture may have any additional amino acid residues other than the aforementioned amino acid residues within a range that does not impair the cell adhesiveness and the adsorbability with respect to the cell culture surface of the support. Examples of the sequence consisting of any additional amino acid residues described above include an additional sequence added for easily preparing the polypeptide for culture by a recombination technique. Examples of the additional sequence include a methionine residue on the N-terminal side, a GPLG sequence on the N-terminal side, a tag sequence (for example, glutathione S-transferase (GST), a FLAG tag, or a His tag), a linker sequence (for example, GGGS, GGGGS, or GGGGGS) which can be added so as to be positioned between the respective domains, and the like.

The polypeptide for culture can be manufactured by an amino acid synthesis technique or a gene recombination technique known to those in the related art.

Specifically, in a case where the polypeptide for culture of the present invention is obtained by the gene recombination technique, first, a gene encoding a target amino acid sequence is obtained, and the polynucleotide of the obtained gene is incorporated into an expression vector, thereby preparing a recombinant expression vector. Thereafter, by introducing the obtained recombinant expression vector into an appropriate host, a transformant is prepared. By culturing the obtained transformant in an appropriate medium, an intended polypeptide is produced. Therefore, by collecting the intended polypeptide from the culture by a common method, the polypeptide according to the present invention can be obtained.

From the viewpoint of the cell growth properties and the ability to grow the undifferentiated pluripotent stem cells in the undifferentiated state, and the like, the polypeptide for culture is preferably a polypeptide (A) which consists of 80 to 450 amino acid residues and includes (1) a first domain including an amino acid sequence consisting of the 25$^{th}$ to 47$^{th}$ amino acid residues of the amino acid sequence represented by SEQ ID NO: 3, (2) at least one domain selected from the group consisting of a second domain, which includes an amino acid sequence consisting of the 342$^{nd}$ to 373$^{rd}$ amino acid residues of the amino acid sequence represented by SEQ ID NO: 3, and the following third and fourth domains, (3) a third domain including an amino acid sequence, which consists of the 269$^{th}$ to 341$^{st}$ amino acid residues of the amino acid sequence represented by SEQ ID NO: 3, or a partial amino acid sequence thereof, and (4) a fourth domain including an amino acid sequence, which consists of the 374$^{th}$ to 459$^{th}$ amino acid residues of the amino acid sequence represented by SEQ ID NO: 3, or a partial amino acid sequence thereof.

Furthermore, from the viewpoint of the cell growth properties, the ability to grow the undifferentiated pluripotent stem cells in the undifferentiated state, and the like, the polypeptide for culture is preferably a polypeptide (B) which consists of 100 to 450 amino acid residues and includes (1) a first domain including an amino acid sequence (including the amino acid sequence represented by SEQ ID NO: 1 and the RGD sequence) consisting of the 1$^{st}$ to 55$^{th}$ amino acid residues of the amino acid sequence represented by SEQ ID NO: 3, (2) at least one domain selected from the group consisting of a second domain (heparin binding domain) including an amino acid sequence, which consists of the 342$^{nd}$ to 373$^{rd}$ amino acid residues of the amino acid sequence represented by SEQ ID NO: 3, and the following third and fourth domains, (3) a third domain including an amino acid sequence, which consists of the 269$^{th}$ to 341$^{st}$ amino acid residues of the amino acid sequence represented by SEQ ID NO: 3, or a partial amino acid sequence thereof, and (4) a fourth domain including an amino acid sequence, which consists of the 374$^{th}$ to 459$^{th}$ amino acid residues of the amino acid sequence represented by SEQ ID NO: 3, and a partial amino acid sequence thereof.

The polypeptide (A) or (B) is preferably a polypeptide having a GRAVY value of −2.0 to −0.95.

The polypeptide (A) preferably consists of 80 to 250 amino acid residues.

The polypeptide (A) is more preferably a polypeptide which has a GRAVY value of −2.0 to −0.95 and consists of 80 to 250 amino acid residues.

The polypeptide (A) is even more preferably a polypeptide which has a GRAVY value of −1.70 to −0.975 and consists of 80 to 250 amino acid residues.

The polypeptide (A) or (B) preferably consists of 100 to 250 amino acid residues.

The polypeptide (A) or (B) is more preferably a polypeptide which has a GRAVY value of −2.0 to −0.95 and consists of 100 to 250 amino acid residues.

The polypeptide (A) or (B) is even more preferably a polypeptide which has a GRAVY value of −1.70 to −0.975 and consists of 100 to 250 amino acid residues.

The polypeptide (A) or (B) is still more preferably a polypeptide which has a GRAVY value of −1.70 to −0.975 and consists of 100 to 170 amino acid residues.

Examples of the polypeptide for culture are shown below, but the present invention is not limited thereto.

TABLE 1

| Amino acid sequence | | | | SEQ ID No. |
|---|---|---|---|---|
| DQESCKGRCT EGFNVDKKCQ CDELCSYYQS CCTDYTAECK PQVTRGDVFT MPEDEPSQEE CEGSSLSAVF EHFAMMQRDS WEDIFELLFW GRTSAGTRQP QFISRDWHGV PGQVDAAMAG RIYISGMAPR PSLAKKQRFR HRNRKGYRSQ RGHSRGRNQN SRRPSRATWL SLFSSEESNL GANNYDDYRM DWLVPATCEP IQSVFFFSGD KYYRVNLRTR RVDTVDPPYP RSIAQYWLGC PAPGHL | | | | 4 |
| DQESCKGRCT EGFNVDKKCQ CDELCSYYQS CCTDYTAECK PQVTRGDVFT MPEDEPRPSL AKKQRFRHRN RKGYRSQRGH SRGRNQN | | | | 5 |
| DQESCKGRCT EGFNVDKKCQ CDELCSYYQS CCTDYTAECK PQVTRGDVFT MPEDEGVPGQ VDAAMAGRIY ISGMAPRPSL AKKQRFRHRN RKGYRSQRGH SRGRNQN | | | | 6 |
| DQESCKGRCT EGFNVDKKCQ CDELCSYYQS CCTDYTAECK PQVTRGDVFT MPEDEQPQFI SRDWHGVPGQ VDAAMAGRIY ISGMAPRPSL AKKQRFRHRN RKGYRSQRGH SRGRNQN | | | | 7 |
| DQESCKGRCT EGFNVDKKCQ CDELCSYYQS CCTDYTAECK PQVTRGDVFT MPEDEFWGRT SAGTRQPQFI SRDWHGVPGQ VDAAMAGRIY ISGMAPRPSL AKKQRFRHRN RKGYRSQRGH SRGRNQN | | | | 8 |
| DQESCKGRCT EGFNVDKKCQ CDELCSYYQS CCTDYTAECK PQVTRGDVFT MPEDESQEES EGSSLSAVFE HFAMMQRDSW EDIFELLFWG RTSAGTRQPQ FISRDWHGVP GQVDAAMAGR IYISGMAPRP SLAKKQRFRH RNRKGYRSQR GHSRGRNQNS RRPSRATWLS LFSSEESNLG ANNYDDYRMD WLVPATSEPI QSVFFFSGDK YYRVNLRTRR VDTVDPPYPR SIAQYWLGSP APGHL | | | | 9 |
| DQESCKGRCT EGFNVDKKCQ CDELCSYYQS CCTDYTAECK PQVTRGDVFT MPEDESQEES EGSSLSAVFE HFAMMQRDSW EDIFELLFWG RTSAGTRQPQ FISRDWHGVP GQVDAAMAGR IYISGMAPRP SLAKKQRFRH RNRKGYRSQR GHSRGRNQN | | | | 10 |
| DQESCKGRCT EGFNVDKKCQ CDELCSYYQS CCTDYTAECK PQVTRGDVFT MPEDESQEES EGSSLSAVFE HFAMMQRDSW EDIFELLFWG RTSAGTRQPQ FISRDWHGVP GQVDAAMAGR IYISGMAPRP SLAKKQRFRH RNRKGYRSQR GHSRGRNQNS RRPSR | | | | 11 |

TABLE 1-continued

| Amino acid sequence | SEQ ID No. |
|---|---|
| DQESCKGRCT EGFNVDKKCQ CDELCSYYQS CCTDYTAECK POVTRGDVFT MPEDESQEES EGSSLSAVFE HFAMMQRDSW EDIFELLFWG RTSAGTRQPQ FISRDWHGVP GQVDAAMAGR IYISGMAPRP SLAKKQRFRH RNRKGYRSQR GHSRGRNQNS RRPSRATWLS LFSSE | 12 |
| DQESCKGRCT EGFNVDKKCQ CDELCSYYQS CCTDYTAECK POVTRGDVFT MPEDESQEES EGSSLSAVFE HFAMMQRDSW EDIFELLFWG RTSAGTRQPQ FISRDWHGVP GQVDAAMAGR IYISGMAPRP SLAKKQRFRH RNRKGYRSQR GHSRGRNQNS RRPSRATWLS LFSSEESNLG ANNYD | 13 |
| DQESCKGRCT EGFNVDKKCQ CDELGSYYQS CCTDYTAECK POVTRGDVFT MPEDESQEES EGSEDIFELL FWGRTSAGTR QPQFISRDWH GVPGQVDAAM AGRIYISGMA PRPSLAKKQR FRHRNRKGYR SQRGHSRGRN QN | 14 |

From the viewpoint of the expression efficiency of the polypeptide for culture as a recombinant protein, the polypeptide for culture may have a methionine residue as an amino acid residue in one position. Examples of preferred polypeptides for culture having a methionine residue in one position include RCP-1 to RCP-11 listed below.

TABLE 2

| | Amino acid sequence | SEQ ID No. |
|---|---|---|
| RCP-1 | MDQESCKGRC TEGFNVDKKC QCDELCSYYQ SCCTDYTAEC KPQVTRGDVF TMPEDEPSQE ECEGSSLSAV FEHFAMMQRD SWEDIFELLF WGRTSAGTRQ PQFISRD-WHG VPGQVDAAMA GRIYISGMAP RPSLAKKQRF RHRNRKGYRS QRGHSRGRNQ NSPRPSRATW LSLFSSEESN LGANNYDDYR MDWLVPATCE PIQSVFFFSG DKYYRVNLRT RRVDTVDPPY PRSIAQYWLG GPAPGHL | 15 |
| RCP-2 | MDQESCKGRC TEGFNVDKKC QCDELCSYYQ SCCTDY-TAEC KPQVTRGDVF TMPEDEPRPS LAKKQRFRHR NRKGYRSQRG HSRGRNQN | 16 |
| RCP-3 | MDQESCKGRC TEGFNVDKKC QCDELCSYYQ SCCTDYTAEC KPQVTRGDVF TMPEDE-GVPG GVDAAMAGRI YISGMAPRPS LAKKQR-FRHR NRKGYRSQRG HSRGRNQN | 17 |
| RCP-4 | MDQESCKGRC TEGFNVDKKC QCDELCSYYQ SCCTDYTAEC KPQVTRGDVF TMPED-EQPQF ISRDWHGVPG QVDAAMAGRI YIS-GMAPRPS LAKKQRFRHR NRKGYRSQRG HSRGRNQN | 18 |

TABLE 2-continued

| | Amino acid sequence | SEQ ID No. |
|---|---|---|
| RCP-5 | MDQESCKGRC TEGFNVDKKC QCDELC-SYYQ SCCTDYTAEC KPQVTRGDVF TMPEDEF-WGR TSAGTRQPQF ISRDWH-GVPG QVDAAMAGRI YISGMAPRPS LAKKQRFRHR NRKGYR-SQRG HSRGRNQN | 19 |
| RCP-6 | MDQESCKGRG TEGFNVDKKC QCDELC-SYYQ SCCTDY-TAEC KPQVTRGDVF TMPEDESQEE SEGSSLSAVF EHFAMMQRDS WEDI-FELLFW GRTSAGTRQP QFISRD-WHGV PGQVDAAMAG RIYISGMAPR PSLAKKQRFR HRNRK-GYRSQ RGHSRGRNQN SRRPSRATWL SLF-SSEESNL GANNYDDYRM DWLVPATSEP IQSVFFF-SGD KYYRVNLRTR RVDTVDPPYP RSIAQY-WLGS PAPGHL | 20 |
| RCP-7 | MDQESCKGRC TEGFNVDKKC QCDELC-SYYQ SCCTDY-TAEC KPQVTRGDVF TMPEDESQEE SEGSSLSAVF EHFAMMQRDS WEDI-FELLFW GRTSAGTRQP QFISRD-WHGV PGQVDAAMAG RIYISGMAPR PSLAKKGRFR HRNRK-GYRSQ RGHSRGRNQN | 21 |
| RCP-8 | MDQESCKGRC TEGFNVDKKC QCDELC-SYYQ SCCTDYTAEG KPQVTRGDVF TMPEDES-GEE VFEHFAMMQR DSWEDIFELL FWGRT-SAGTR QPQFISRDWH GVPGQVDAAM AGRIYIS-GMA PRPSLAKKQR FRHRNRKGYR SQRGHSR-GRN QNSRRPSR | 22 |
| RCP-9 | MDQESCKGRC TEGFNVDKKC QCDELC-SYYQ SCCTDY-TAEC KPQVTRGDVF TMPEDESQEE SEGSSLSAVF EHFAMMQRDS WEDI-FELLFW GRTSAGTRQP QFISRD-WHGV PGQVDAAMAG RIYISGMAPR PSLAKKQRFR HRNRK-GYRSQ RGHSRGRNQN SRRPSRATWL SLFSSE | 23 |
| RCP-10 | MDQESCKGRC TEGFNVDKKC QCDELC-SYYQ SCCTDYTAEC KPQVTRGDVF TMPED-EQEES EGSSLSAVFE HFAMMQRDSW EDIFELL-FWG RTSAGTRQPQ FISRDWH-GVP GQVDAAMAGR IYISGMAPRP SLAKKQRFRH RNRKGYR-SQR GHSRGRN-QNS RRPSRATWLS LFSSEESNLG ANNYD | 24 |

TABLE 2-continued

| | Amino acid sequence | SEQ ID No. |
|---|---|---|
| RCP-11 | MDQESCKGRC TEGFNVDKKC QCDELC-SYYQ SCCTDY-TAEC KPQVTRGDVF TMPEDESQEE SEGSEDIFEL LFWGRT-SAGT RQPQFISRDW HGVPGQVDAA MAGRI-YISGM APRPSLAKKG RFRHRNRKGY RSQRGHSRGR NQN | 25 |

The polypeptide for culture is preferably at least one polypeptide selected from the group consisting of (a) a polypeptide having an amino acid sequence represented by any of SEQ ID NO: 4 to SEQ ID NO: 25 (hereinafter, referred to as a "polypeptide (a)"), (b) a polypeptide having an amino acid sequence, which is formed by the deletion, substitution, or addition of one amino acid residue or several amino acid residues in an amino acid sequence represented by any of SEQ ID NO: 4 to SEQ ID NO: 25, and exhibiting adsorbability with respect to the cell culture surface of the support (hereinafter, referred to as a "polypeptie (b)"), and (c) a polypeptide having an amino acid sequence, which shares sequence identity of equal to or higher than 80% with the amino acid sequence represented by any of SEQ ID NO: 4 to SEQ ID NO: 25, and exhibiting adsorbability with respect to the cell culture surface of the support (hereinafter, referred to as a "polypeptide (c)").

The polypeptide (c) is more preferably a polypeptide having an amino acid sequence, which shares sequence identity of equal to or higher than 90% with the amino acid sequence represented by any of SEQ ID NO: 4 to SEQ ID NO: 25, and exhibiting adsorbability with respect to the cell culture surface of the support, and even more preferably a polypeptide having an amino acid sequence, which shares sequence identity of equal to or higher than 95% with the amino acid sequence represented by any of SEQ ID NO: 4 to SEQ ID NO: 25, and exhibiting adsorbability with respect to the cell culture surface of the support.

Furthermore, the polypeptide for culture is preferably at least one polypeptide selected from the group consisting of (a-1) a polypeptide including an amino acid sequence represented by any of SEQ ID NO: 4 to SEQ ID NO: 25 (hereinafter, referred to as a "polypeptide (a-1)"), (b-1) a polypeptide including an amino acid sequence, which is formed by the deletion, substitution, or addition of one amino acid residue or several amino acid residues in the amino acid sequence represented by any of SEQ ID NO: 4 to SEQ ID NO: 25, and exhibiting adsorbability with respect to the cell culture surface of the support (hereinafter, referred to as a "polypeptide (b-1)"), and (c-1) a polypeptide including an amino acid sequence, which shares sequence identity of equal to or higher than 80% with the amino acid sequence represented by any of SEQ ID NO: 4 to SEQ ID NO: 25, and exhibiting adsorbability with respect to the cell culture surface of the support (hereinafter, referred to as a "polypeptide (c-1)").

The polypeptide (c-1) is more preferably a polypeptide including an amino acid sequence, which shares sequence identity of equal to or higher than 90% with the amino acid sequence represented by any of SEQ ID NO: 4 to SEQ ID NO: 25, and exhibiting adsorbability with respect to the cell culture surface of the support, and even more preferably a polypeptide including an amino acid sequence, which shares sequence identity of equal to or higher than 95% with the amino acid sequence represented by any of SEQ ID NO: 4 to SEQ ID NO: 25, and exhibiting adsorbability with respect to the cell culture surface of the support.

In the amino acid sequences of the polypeptides (b) and (b-1), a single amino acid residue or several amino acid residues may undergo deletion, substitution, or addition and the number of such amino acid residues varies with the total number of amino acid residues of the polypeptide. The number of such amino acid residues can be, for example, 2 to 15 and preferably 2 to 5.

The phrase "in the presence of the polypeptide for culture" means that the polypeptide for culture should be present in the culture system of the pluripotent stem cells. It is preferable that the polypeptide for culture coats the cell culture surface of the support. In a case where the support is made of polystyrene having a plasma-treated cell culture surface, the plasma-polymerized thin film formed by the plasma treatment should be coated with the polypeptide for culture. As the method for forming the plasma-polymerized thin film on the cell culture surface, a common method should be used as it is.

One kind of polypeptide for culture may be present singly during the culture of the pluripotent stem cells, or two or more kinds thereof may be present in combination during the culture.

The cell culture surface coated with the polypeptide for culture can be obtained by preparing an adsorbent solution containing the polypeptide for culture in a predetermined amount, applying the prepared adsorbent solution onto the cell culture surface, and holding the cell culture surface as it is for a certain period of time. Within the cell culture surface to which the adsorbent solution is applied, the polypeptide for culture contained in the adsorbent solution can coat the cell culture surface by being adsorbed onto the cell culture surface. Herein, within a range that does not impair the effects of the present invention, the cell culture surface may have a portion not coated with the polypeptide for culture. The polypeptide for culture can preferably coat about 75% or more of the cell culture surface and more preferably coat about 85% or more of the cell culture surface.

The content of the polypeptide for culture in the adsorbent solution varies with the type or size of the culture surface onto which the polypeptide is adsorbed, and can be appropriately adjusted. From the viewpoint of the adsorbability of the polypeptide for culture with respect to the culture surface, the amount of the polypeptide for culture applied onto the cell culture surface is preferably 1 pmol/cm$^2$ to 1,000 pmol/cm$^2$, and more preferably 100 pmol/cm$^2$ to 300 pmol/cm$^2$. An aqueous medium used for preparing the adsorbent solution is not particularly limited, and examples thereof include a phosphate buffer solution, a tris-buffer solution, ultrapure water, and the like.

After the adsorbent solution is applied, the polypeptide for culture should be allowed to be adsorbed onto the cell culture surface by being held as it is for a certain period of time, for example, for about 30 minutes to 24 hours. In this way, the polypeptide for culture can be adsorbed onto the cell culture surface without the need to perform a special treatment.

<Medium>

The medium used for pluripotent stem cell culture is a medium in which the concentration of 2-mercaptoethanol is equal to or less than 10 That is, the medium used for pluripotent stem cell culture is a medium in which the concentration of 2-mercaptoethanol is 0 μM to 10 μM.

If the concentration of 2-mercaptoethanol is controlled to become equal to or less than 10 μM (μmol/L), the pluripotent stem cells can efficiently grow in an undifferentiated state. In the present invention, the concentration of 2-mercaptoethanol in the medium is preferably equal to or less than 9.0 μM (that is, the concentration of 2-mercaptoethanol in the medium in the present invention is preferably 0 μM to 9.0 μM) and particularly preferably 0 μM. That is, it is particularly preferable to use a medium not containing 2-mercaptoethanol.

Other components of the medium are not particularly limited as long as the content of 2-mercaptoethanol in the medium is equal to or less than 10 μM, and the media generally used for pluripotent stem cell culture can be used.

The medium used for culture can be appropriately selected according to the type of cells to be cultured. Any of known media can be used, and examples thereof include media such as DMEM, MEM, F 12, DME, RPMI 1640, MCDB 104 and 199, MCDB 153, L 15, SkBM, and Basal. Furthermore, to these culture solutions, various components that can be generally added, for example, glucose and antibiotics (penicillin, streptomycin, and the like) can be added. From the viewpoint of controlling the quality of components of the medium and ensuring the safety of the cultured cells, the medium is preferably a serum-free medium not containing serum such as fetal bovine serum (FBS) or human serum.

It is preferable that the pluripotent stem cells are cultured in the absence of a heterogeneous animal-derived component. In this way, a likelihood of the intermixing of a heterogeneous animal-derived foreign substance can be eliminated with high accuracy. Examples of the culture of pluripotent stem cells in the absence of a heterogeneous cell-derived component include the culture using a medium not containing a heterogeneous animal-derived component, the culture not using a heterogeneous animal-derived feeder cells, and the like.

Furthermore, it is preferable that the pluripotent stem cells are cultured in the absence of a heterogeneous animal-derived component and a serum component. In this way, the intermixing of a heterogeneous animal-derived component can be more reliably prevented.

As the culture solution not containing a heterogeneous animal-derived component, it is possible to use a medium mixture composed of a hypoosmotic medium containing at least one kind of generally used medium component such as water; a salt including an inorganic salt such as sodium, potassium, magnesium, or calcium and an organic salt such as sodium pyruvate; an amino acid including an essential amino acid and a nonessential amino acid; vitamin such as L-ascorbic acid, riboflavin, biotin, or cyanocobalamin; a trace element such as selenium, iron, zinc, copper, manganese, nickel, or cadmium; a carbon source such as D-glucose; FGF such as a basic fibroblast growth factor (FGF)-2; and a factor such as a transforming growth factor (TGF)-β, insulin, and transferrin.

Particularly, a medium is preferable which contains water, a salt (an inorganic salt such as sodium, potassium, magnesium, or calcium and an organic salt such as sodium pyruvate), an amino acid (an essential amino acid and a nonessential amino acid), vitamin (L-ascorbic acid, riboflavin, biotin, cyanocobalamin, or the like), a trace elements (selenium, iron, zinc, copper, or the like), a carbon source (D-glucose or the like), FGF (basic fibroblast growth factor FGF-2 or the like), TGF-β, insulin, and transferrin. From the viewpoint of efficiently growing the pluripotent stem cells in an undifferentiated state, a medium containing FGF is preferable, and a medium containing FGF and TGF-β is more preferable. Specifically, examples of the medium include Essential 8 (trade name, will not be mentioned hereinafter, Life Technologies), NurtiStem (registered trademark, will not be mentioned hereinafter, Biological Industries, Ltd.), and the like. Among these, Essential 8 (Life Technologies) is particularly preferable because it does not contain a serum component and is excellent the growth efficiency of the pluripotent stem cells.

Essential 8 which is a particularly preferred medium contains only eight basic components. Specifically, it is a medium prepared by adding sodium hydrogen carbonate, selenium, insulin, transferrin, L-ascorbic acid, a basic fibroblast growth factor (FGF-2), and a transforming growth factor (TGF-β) to DMEM/F12 which is a basic medium at a predetermined concentration. Essential 8 can be purchased from Life Technologies and Stemcell Technologies Inc, and may also be prepared by mixing the respective constituents together.

The cells are cultured in an incubator under general culture conditions, for example, a temperature of 37° C. and a $CO_2$ concentration of 5% (v/v).

The aforementioned medium can be preferably used in the subculture method of the pluripotent stem cells. Furthermore, the pluripotent stem cells are seeded into the medium by a common method. Herein, it is not necessary to use the same medium for a series of passages, and as long as the pluripotent stem cells can be kept undifferentiated, different media may be used.

The seeding density and the culture conditions of the pluripotent stem cells are not particularly limited, and generally used conditions can be used as they are. For example, the cells may be seeded at a seeding density of about $1 \times 10^3$ cells/cm$^2$ to $1 \times 10^5$ cells/cm$^2$ and cultured under the aforementioned culture and subculture conditions. Furthermore, a cell mass with a diameter of 10 μm to 100 μm may be seeded at a seeding density of about 1 cell/cm$^2$ to 5 cells/cm$^2$ and cultured under the aforementioned culture and subculture conditions.

The culture method for the pluripotent stem cells may further include a step of obtaining a polypeptide-coated cell culture surface of the support by applying the polypeptide for culture onto the cell culture surface of the support. As the method for applying the polypeptide for culture onto the cell culture surface of the support, a method may be used in which an adsorbent solution containing the polypeptide for culture is prepared and applied to the cell culture surface of the support. The adsorbent solution containing the polypeptide for culture and the conditions under which the polypeptide is applied by the method using the adsorbent solution are as described above.

According to the culture method of the present invention, it is possible to keep the pluripotent stem cells undifferentiated and induce high growth activity for the pluripotent stem cells. Therefore, the culture method of the present invention is preferably used at the time of culturing the pluripotent stem cells, particularly, at the time of culturing the pluripotent stem cells for a long period of time.

The culture kit of the present invention is a culture kit for pluripotent stem cells including the polypeptide for culture and the medium in which the concentration of 2-mercaptoethanol is equal to or less than 10 According to the culture kit of the present invention, it is possible to conveniently perform the culture method for pluripotent stem cells of the present invention.

The polypeptide for culture and the medium in which the concentration of 2-mercaptoethanol is equal to or less than 10 μM are as described above.

If necessary, the kit of the present invention can include other constituents. Examples of other constituents include a support, a cell exfoliating agent, a cell exfoliating instrument, an instruction manual describing the culture method of the present invention, and the like. Regarding the support as one of other constituents contained in the kit, the details described above in relation to the culture method can be applied as they are.

In a case where the kit of the present invention includes a support, the polypeptide for culture may be included in the kit separately from the support or may be included in the kit by being applied onto the cell culture surface of the support.

EXAMPLES

Hereinafter, the present invention will be specifically described based on examples, but the present invention is not limited thereto. Herein, unless otherwise specified, "%" is based on mass.

Reference Examples

Preparation of Polypeptide

1. Preparation of Polypeptide for Culture

By a common method using PCR, gene sequences encoding each of the polypeptides RCP-1 to RCP-11 having the amino acid sequences shown in Table 3 were amplified. In Table 3, the numerical values in the column of "NOTE" show the position in the amino acid sequence (SEQ ID NO: 3) of natural human vitronectin corresponding to the amino acid sequence of each of the polypeptides.

For RCP-1 to RCP-11, target genes were inserted into pET-28b(+), which was cleaved in advance by being treated with NcoI (TAKARA BIO INC.), by using an InFusion Advantage PCR Cloning Kit (Clontech Laboratories, Inc), thereby constructing the respective expression vectors. The sequences of the expression vectors were checked by sequence analysis.

TABLE 3

| | Amino acid sequence | | | SEQ ID No. | NOTE |
|---|---|---|---|---|---|
| RCP-1 | MDQESCKGRC | TEGFNVDKKC | QCDELCSYYQ | 15 | 1-55 |
| | SCCTDYTAEC | KPQVTRGDVF | TMPEDEPDQE | | 269-459 |
| | ECEGSSLSAV | FEHFAMMQRD | SWEDIFELLF | | |
| | WGRTSAGTRQ | PQFISRDWHG | VPGQVDAAMA | | |
| | GRIYISGMAP | RPSLAKKQRF | RHNRKGYRSQ | | |
| | RGHSRGRNQN | SRRPSRATWL | SLFSSEESNL | | |
| | GANNYDDYRM | DWLVPATCEP | IQSVFFFSGD | | |
| | KYYRVNLRTR | RVDTVDPPYF | RSIAQYWLGC | | |
| | PAPGHL | | | | |
| RCP-2 | MDQESCKGRC | TEGFNVDKKC | QCDELCSYYQ | 16 | 1-55 |
| | SCCTDYTAEC | KPQVTRGDVF | TMPEDEPRPS | | 342-373 |
| | LAKKQRFRHR | NRKGYRSQRG | HSRGRNQN | | |
| RCP-3 | MDQESCKGRC | TEGFNVDKKC | QCDELCSYYQ | 17 | 1-55 |
| | SCCTDYTAEC | KPQVTRGDVF | TMPEDEGVPG | | 322-341 |
| | QVDAAMAGRI | YISGMAPRPS | LAKKQRFRHR | | 342-373 |
| | NRKGYRSQRG | HSRRNQNG | | | |

TABLE 3-continued

| | Amino acid sequence | | | SEQ ID No. | NOTE |
|---|---|---|---|---|---|
| RCP-4 | MDQESCKGRC | TEGFNVDKKC | QCDELCSYYQ | 18 | 1-55 |
| | SCCTDYTAEC | KPQVTRGDVF | TMPEDEQPQF | | 312-341 |
| | ISRDWHGVPG | QVDAAMAGRI | YISGMAPRPS | | 342-373 |
| | LAKKQRFRHR | NRKGYRSQRG | HSRGRNQN | | |
| RCP-5 | MDQESCKGRC | TEGFNVDKKC | QCDELCSYYQ | 19 | 1-55 |
| | SCCTDYTAEC | KPQVTRGDVF | TMPEDEFWGR | | 302-341 |
| | TSAGTRQPQF | ISRDWHGVPG | QVDAAMAGRI | | 342-373 |
| | YISGMAPRPS | LAKKQRFRHR | NRKGYRSQRG | | |
| | HSRGRNQN | | | | |
| RCP-6 | MDQESCKGRC | TEGFNVDKKC | QCDELCSYYQ | 20 | 1-55 |
| | SCCTDYTAEC | KPQVTRGDVF | TMPEDESQEE | | 269-459 |
| | SEGSSLSAVF | EHFAMMQRDS | WEDIFELLFW | | C274S |
| | GRTSAGTRQP | QFISRDWHGV | PGQVDAAMAG | | |
| | RIYISGMAPR | PSLAKKQRFR | HRNRKGYRSQ | | |
| | RGHSRGRNQN | SRRPSRATWL | SLFSSEESNL | | |
| | GANNYDDYRM | DWLVPATSEP | IQSVFFFSGD | | |
| | KYYRVNLRTR | RVDTVDPPYP | RSIAQYWLGS | | |
| | PAPGHL | | | | |
| RCP-7 | MDQESCKGRC | TEGFNVDKKC | QCDELCSYYQ | 21 | 1-55 |
| | SCCTDYTAEC | KPQVTRGDVF | TMPEDESQEE | | 269-373 |
| | SEGSSLSAVF | EHFAMMQRDS | WEDIFELLFW | | C274S |
| | GRTSAGTRQP | QFISRDWHGV | PGQVDAAMAG | | |
| | RIYISGMAPR | PSLAKKQRFR | HRNRKGYRSQ | | |
| | RGHSRGRNQN | | | | |
| RCP-8 | MDQESCKGRC | TEGFNVDKKC | QCDELCSYYQ | 22 | 1-55 |
| | SCCTDYTAEC | KPQVTRGDVF | TMPEDESQEE | | 269-373 |
| | SEGSSLSAVF | EHFAMMQRDS | WEDIFELLFW | | 374-379 |
| | GRTSAGTRQP | QFISRDWHGV | PGQVDAAMAG | | C274S |
| | RIYISGMAPR | PSLAKKQRFR | HRNRKGYRSQ | | |
| | RGHSRGRNQN | SRRPSR | | | |
| RCP-9 | MDQESCKGRC | TEGFNVDKKC | QCDELCSYYQ | 23 | 1-55 |
| | SCCTDYTAEC | KPQVTRGDVF | TMPEDESQEE | | 269-373 |
| | SEGSSLSAVF | EHFAMMQRDS | WEDIFELLFW | | 374-389 |
| | GRTSAGTRQP | SFISRDWHGV | PGQVDAAMAG | | C274S |
| | RIYISGMAPR | PSLAKKQRFR | HRNRKGYRSQ | | |
| | RGHSRGRNQN | SRRPSRATWL | SLFSSE | | |
| RCP-10 | MDQESCKGRC | TEGFNVDKKC | QCDELCSYYQ | 24 | 1-55 |
| | SCCTDYTAEC | KPQVTRGDVF | TMPEDESQEE | | 269-373 |
| | SEGSSLSAVF | EHFAMMQRDS | WEDIFELLFW | | 374-399 |
| | GRTSAGTRQP | SFISRDWHGV | PGQVDAAMAG | | C274S |
| | RIYISGMAPR | PSLAKKQRFR | HRNRKGYRSQ | | |
| | RGHSRGRNQN | SRRPSRATWL | SLFSSEESNL | | |
| | GANNYD | | | | |
| RCP-11 | MDQESCKGRC | TEGFNVDKKC | QCDELCSYYQ | 25 | 1-55 |
| | SCCTDYTAEC | KPQVTRGDVF | TMPEDESQEE | | 269-277 |
| | SEGSEDIFEL | LFWGRTSAGT | RQPQFISRDW | | 295-341 |
| | HGVPGQVDAA | MAGRIYISGM | APRPSLAKKQ | | 342-373 |
| | RFRHRNRKGY | RSQRGHSRGR | NQN | | C274S |

The prepared expression vectors of RCP-1 to RCP-11 were transformed into BL21(DE3)pLysS (Novagen) by a common method, applied to a kanamycin-containing LB plate, and incubated for 16 hours at 37° C. By a colony direct PCR method, the state where the vectors were introduced into the cells was checked. Thereafter, 1 mM isopropyl-β-

D-thiogalactopyranoside (IPTG, Wako Pure Chemical Industries, Ltd.) was added thereto, and the cells were cultured by being shaken for 5 hours at 37° C., thereby inducing the expression of the polypeptides.

The bacterial cells were collected through a centrifugal treatment and resuspended in a washing buffer (20 mM Tris, 150 mM NaCl, pH 7.6). Through sonication, the bacterial cells were fragmented and then subjected to centrifugation for 30 minutes at 4° C. and 15,000 rpm, and an insoluble fraction was collected. The bacterial cells were washed with a washing buffer containing 0.5% by mass of Triton×100, then resuspended in a low-concentration urea buffer (Low Urea Buffer: 20 mM Tris, 150 mM NaCl, 2 M urea, pH 7.6), and subjected to a sonication treatment. Through a centrifugation treatment, an insoluble fraction was collected, a high-concentration urea buffer (High Urea Buffer: 20 mM Tris, 150 mM NaCl, 8 M urea, pH 7.6) was then added thereto, and the insoluble fraction was solubilized through a sonication treatment.

The solution obtained by the method described above that contained a target peptide was purified by using AKTA Explorer 100 (GE Healthcare Japan Corporation) and HiTrap Heparin HP 5 ml (GE Healthcare Japan Corporation). By performing stepwise elution using a high-concentration urea buffer as a binding buffer and a high-salt concentration adjusting buffer (20 mM Tris, 1 M NaCl, 8 M urea, pH 7.6) as an elution buffer, the target polypeptide was purified.

2. Preparation of Comparative Polypeptide

As comparative polypeptides, expression vectors of the following RCP-21 to RCP-26 were constructed by inserting target genes in the same manner as used for RCP-1 to RCP-11, except that pGEX-6P-1 (GE Healthcare Japan Corporation) cleaved in advance by being treated with BamHI (TAKARA BIO INC.) was used. Herein, RCP-11 corresponds to the sequence of natural human vitronectin. In Table 4, the numerical values in the column of "NOTE" show the position in the amino acid sequence (SEQ ID NO: 3) of the natural human vitronectin corresponding to the amino acid sequence of each of the polypeptides.

TABLE 4

| | Sequence | | | SEQ ID NO | NOTE |
|---|---|---|---|---|---|
| RCP-21 | GPLGDQESCK | GRCTEGFNVD | KKC-QCDELCS | 26 | 1-459 |
| | YYQSCCTDYT | AECKPQVTRG | DVFTM-PEDEY | | |
| | TVYDDGEEKN | NATVHEQVGG | PSLTS-DLQAQ | | |
| | SKGNPEQTPV | LKPEEEAPAP | EVGASK-PEGI | | |
| | DSRPETLHPG | RPQPPAEEEL | CSGK-PFDAFT | | |
| | DLKNGSLFAF | RGQYCYELDE | KAVRP-GYPKL | | |
| | IRDVWGIEGP | IDAAFTRINC | QGK-TYLFKGS | | |
| | QYWRFEDGVL | DPDYPRNISD | GFDGIPD-NVD | | |
| | AALALPAHSY | SGRERVYFFK | GKQYWEY-QFQ | | |
| | HQPSQEECEG | SSLSAVFEHF | AMMQRD-SWED | | |
| | IFELLFWGRT | SAGTRQPQFI | SRDWH-GVPGQ | | |
| | VDAAMAGRIY | ISGMAPRPSLA | KKQR-FRHRN | | |
| | RKGYRSQRGH | SRGRNQN-SRR | PSRATWLSLF | | |
| | SSEESNLGAN | NYDDYRMDWL | VPAT-CEPIQS | | |
| | VFFFSGDKYY | RVNLRTRRVD | TVDPPY-PRSI | | |
| | AQYWLGCPAP | GHL | | | |
| RCP-22 | GPLGDQESCK | GRCTEGFNVD | KKC-QCDELCS | 27 | 1-55 |
| | YYQSCCTDYT | AECKPQVTRG | DVFTM-PEDEY | | |
| | TVYDDGEEKN | NATVHEQVGG | PSLTS-DLQAQ | | 56-268 |
| | SKGNPEQTPV | LKPEEEAPAP | EVGASK-PEGI | | |
| | DSRPETLHPG | RPQPPAEEEL | CSGK-PFDAFT | | |
| | DLKNGSLFAF | RGQYCYELDE | KAVRP-GYPKL | | |
| | IRDVWGIEGP | IDAAFTRINC | QGK-TYLFKGS | | |
| | QYWRFEDGVL | DPDYPRNISD | GFDGIPD-NVP | | |
| | AALALPAHSY | SGRERVYFFK | GKQYWEY-QFQ | | |
| | HQ | | | | |
| RCP-23 | GPLGDQESCK | GRCTEGFNVD | KKC-QCDELCS | 28 | 1-55 |
| | YYQSCCTDYT | AECKPQVTRG | DVFTM-PEDEY | | |
| | TVYDDGEEKN | NATVHEQVGG | PSLTS-DLQAQ | | 56-129 |
| | SKGNPEQTPV | LKPEEEAPAP | EVGASK-PEGI | | |
| | DSRPETLHPG | RPQP | | | |
| RCP-24 | GPLGDQESCK | GRCTEGFNVD | KKC-QCDELCS | 29 | 1-55 |
| | YYQSCCTDYT | AECKPQVTRG | DVFTMPEDE | | |
| RCP-25 | QPLGYTVYDD | GEEKNNATVH | EQVG-GPSLTS | 30 | 56-459 |
| | DLQAQSKGNP | EQTPVLKPEE | EAPAPEV-GAS | | |
| | KPEGIDSRPE | TLHPGRPQPP | AEEELC-SGKP | | |
| | FDAFTDLKNG | SLFAFRGQYC | YELDEKA-VRP | | |
| | GYPKLIRDVW | GIEGPIDAAF | TRINCQG-KTY | | |
| | LFKGSQYWRF | EDGVLDPDYP | RNIS-DGFDGI | | |
| | PDNVDAALAL | PAHSYSGRER | VYFFKG-KQYW | | |
| | EYQFQHQPSQ | EECEGSSLSA | VFEHFAM-MQR | | |
| | DSWEDIFELL | FWGRT-SAGTR | QPQFISRDWH | | |
| | GVPGQVDAAM | AGRIYISGMA | PRPSLAK-KQR | | |
| | FRHRNRKGYR | SQRGHSRGRN | QNSR-RPSRAT | | |
| | WLSLFSSEES | NLGANNYDDY | RMDWLV-PATC | | |
| | EPIQSVFFFS | GDKYYRVNLR | TRRVDT-VDPP | | |
| | YPRSIAQYWL | GCPAPGHL | | | |
| RCP-26 | GPLGPSQEEC | EGSSLSAVFE | HFAM-MQRDSW | 31 | 269-459 |
| | EDIFELLFWG | RTSAGTRQPQ | FISRD-WGVPG | | |
| | QVDAAMAGRI | YISGMAPRPS | LAKKQR-FRHR | | |
| | NRKGYRSQRG | HSRGRN-QNSR | RPSRATWLSL | | |
| | FSSEESNLGA | NNYDDYRMDW | LVPAT-CEPIQ | | |
| | SVFFFSGDKY | YRVNLRTRRV | DTVDPPY-PRS | | |
| | IAQYWLGCPA | PGHL | | | |

The expression vectors of RCP-21 to RCP-26 prepared as above were transformed into BL21 (Novagen) by a common method, applied to an ampicillin-containing LB plate, and incubated for 16 hours at 37° C. By a colony direct PCR method, the state where the vectors were introduced into the cells was checked. Thereafter, 100 μM IPTG was added thereto, and the cells were cultured by being shaken for 24 hours at 20° C., thereby inducing the expression of the polypeptides.

The bacterial cells were collected by a centrifugation treatment, resuspended in a B-PER (registered trademark)

Bacterial Protein Extraction Reagent in Phosphate Buffer (Thermo Fisher Scientific Inc.), and then fragmented through sonication. By performing centrifugation for 30 minutes at 4° C. and 15,000 rpm, an insoluble fraction was removed, and the supernatant was purified by using AKTA Explorer 100 and GSTrap HP 5 ml×2 (GE Healthcare Japan Corporation). The eluted fraction was desalted by using Hiprep 26/10 Desalting (GE Healthcare Japan Corporation). Furthermore, a protease (PreScission Protease) for cleaving a glutathione S transferase (GST)-fusion protein was added thereto in a solution amount of ½,₀₀₀, and the resultant was incubated for 24 hours at 4° C., thereby cleaving the GST tag. The resultant was purified again by using GSTrap HP 5 ml×2, and the cleaved GST tag was removed by being adsorbed onto a column. The fraction passing through the column was dialyzed using Slide-A-Lizer (3.5 K MWCO: Thermo Fisher Scientific Inc., the same device will be used hereinafter) and substituted with PBS.

3. Analysis of Properties of Polypeptide for Culture
<GRAVY Value and Aggregation Characteristics>

The polypeptide of RCP-1 obtained as above was subjected to electrophoresis by using Ready Gel (12.5%, Bio-Rad Laboratories, Inc.) and stained with a GelCode™ Blue Stain Reagent (Thermo Scientific). As a result, a single band could be confirmed at a site corresponding to a molecular weight of 28.3 kDa expected from the amino acid sequence. The same results were obtained from other polypeptides.

For RCP-1 to RCP-11, each of the purified polypeptide solutions was dialyzed using Slide-A-Lizer (3.5 K MWCO.). Basically, by using a dialysis buffer (PBS, 1.5 M NaCl, 0.5 M L-arginine, 1 mM EDTA, pH 7.4) as an outer dialysate, urea was removed by stepwise dialysis. The concentration of the end-product of dialysis was calculated from the absorbence at 280 nm by using NanoDrop (Thermo Fisher Scientific Inc.). Table 5 shows whether or not aggregation occurred after dialysis.

Furthermore, the indices of hydrophobicity determined for each of the amino acids were summed up, the obtained value was divided by the number of the amino acids, and the outcome was determined as the GRAVY value (see Kyte J., Doolittle R. F. (1982), J. Mol. Biol, 157: 105-132). The GRAVY value is an index of the hydrophilicity and hydrophobicity of a polypeptide calculated from the degree of hydrophobicity of the amino acids contained in each polypeptide. The greater the GRAVY value, the more the polypeptide is hydrophobic, and the smaller the GRAVY value, the more the polypeptide is hydrophilic. The results are shown in Table 5.

Whether or not aggregation was occurred was evaluated based on the scale of A, and B as shown below. The results are summarized in Table 5.

G: The formation of an aggregate was not observed.
A: The formation of particles having a particle size of about 100 nm was observed.
B: The formation of an aggregation of particles having a particle size of equal to or greater than 1 mm was visually observed.

TABLE 5

|  | GRAVY | Number of amino acids | Aggregation |
| --- | --- | --- | --- |
| RCP-1 | −0.835 | 247 | A |
| RCP-2 | −1.516 | 88 | G |
| RCP-3 | −1.124 | 108 | G |
| RCP-4 | −1.150 | 118 | G |
| RCP-5 | −1.124 | 128 | G |

TABLE 5-continued

|  | GRAVY | Number of amino acids | Aggregation |
| --- | --- | --- | --- |
| RCP-6 | −0.875 | 246 | A |
| RCP-7 | −0.979 | 160 | A |
| RCP-8 | −1.045 | 166 | A |
| RCP-9 | −0.958 | 176 | B |
| RCP-10 | −0.971 | 186 | B |
| RCP-11 | −1.072 | 143 | A |

From Table 5, it is understood that RCP-2 to RCP-5, RCP-7, RCP-8, and RCP-11 are polypeptides consisting of about 80 to 170 amino acid residues and are easily aggregated, but because they have a GRAVY value of −1.70 to −0.975, the polypeptides are inhibited from forming an aggregate.

<Evaluation of Adsorbability with Respect to Cell Culture Surface>

Each of the polypeptides of RCP-1 to RCP-11 and RCP-21 to RCP-26 obtained as above was diluted with a predetermined buffer such that they could be added to wells at a predetermined final concentration of 0 pmol/cm² to 200 pmol/cm². Thereafter, each of the polypeptides was added in an amount of 64 μL to a plasma-treated 96-well plate made of polystyrene (Tissue Culture-Treated, Falcon). Each of the polypeptides was allowed to adsorb onto the plate by being incubated for 2 hours at 37° C., and then the wells were washed twice with PBS, thereby obtaining surfaces coated with each of the polypeptides of RCP-1 to RCP-11 and RCP-21 to RCP-26.

Among the surfaces coated with each of the polypeptides obtained as above, the surfaces coated with RCP-1 and RCP-21 to RCP-26 were applied with 64 μL of a borate buffer and 64 μL of 1 N NaOH, followed by incubation for 24 hours at 80° C. and 100% humidity. After the resultant was air-cooled, 75 μL of a borate buffer was added to each well, and 50 μL of a reaction solution obtained by mixing OPA (o-phthalaldehyde: Wako Pure Chemical Industries, Ltd./methanol solution (160 mg/ml)) with N-acetyl-L-cysteine (NAC: Wako Pure Chemical Industries, Ltd.)/borate buffer solution (2 mg/ml) at a ratio of 1:100 (mass ratio) was further added thereto. After incubation for 30 minutes at 40° C., the fluorescence intensity thereof was measured by using an Envision Multilabel Counter (PerkinElmer Inc.) (excitation 355 nm/fluorescence 486 nm). A calibration curve was separately prepared from each of the polypeptide solutions so as to calculate the amount of the polypeptide adsorbed. The results are shown in FIG. 1. In FIG. 1, a black rhombus indicates RCP-1, a black square indicates RCP-21, a black triangle indicates RCP-22, a black circle indicates RCP-23, a white rhombus indicates RCP-24, a white square indicates RCP-25, and a white triangle indicates RCP-26.

From FIG. 1, it is understood that among the polypeptides used in the test, the polypeptides of RCP-1, RCP-25, and RCP-26 including PRPSLAKKQRFRHRNRKGYR-SQRGHSRGRNQN (SEQ ID NO: 2 [the 342$^{nd}$ to 373$^{rd}$ amino acids in SEQ ID NO: 3]) exhibit excellent adsorbability with respect to the plate that is equivalent to the adsorbability of RCP-21 having the sequence of human vitronectin. It is also understood that, in contrast, the amount of RCP-23 and RCP-24 not including PRPSLAKKQR-FRHRNRKGYRSQRGHSRGRNQN adsorbed onto the plate is about ¼ of the amount of the polypeptides containing the aforementioned sequence adsorbed onto the plate, and thus RCP-23 and RCP-24 are inappropriate as materials to be adsorbed onto the cell culture surface.

<Cell Adhesiveness Evaluation 1>

The cell adhesiveness of human iPS cells ("Tic": Cell No. JCRB 1331: from National Institute of Biomedical Innovation. [567-0085, 7-6-8 Asagi Saito Ibaraki-City Osaka]) with respect to the aforementioned polypeptides was evaluated in the following manner.

As feeder cells for retaining the human iPS cells, Embryo-Max (registered trademark) (early mouse embryonic fibroblasts: resistant to hygromycin, treated with mitomycin C, derived from C57/BL6, third passage) (Millipore Corporation) was used. By using DMEM (Invitrogen) and a 10% (v/v) fetal bovine serum medium, the feeder cells were cultured for 24 hours and attached to a T25 flask (Corning Incorporated). As a medium for the human iPS cells, the one obtained by adding FGF-2 (Sigma-Aldrich Co, LLC.) to a medium composed as shown in Table 6 at a final concentration of 10 ng/ml was used.

TABLE 6

| Composition | Manufacturer | Amount |
|---|---|---|
| KO-DMEM/F12 | Invitrogen | 400 ml |
| Non-Essential Amino Acid Solution | | 4 ml |
| L-Glutamine | | 5 ml |
| Knock Out Serum Replacement | | 100 ml |
| 2-mercaptoethanol 55 mM | Wako Pure Chemical Industries, Ltd. | 0.925 ml |

Total amount: about 500 ml

By using the aforementioned medium, the human iPS cells were retained and cultured in a 5% (v/v, the same unit will be used hereinafter) $CO_2$ incubator at 37° C. Except for the day after the seeding of the iPS cells, the medium was replaced every day. The subculture operation was performed by exfoliating the cells by using Dispase II (neutral protease Grade II, Roche) and separating the cells in an appropriate size by a pipetting operation.

The iPS cells cultured as described above were treated with TrypLE Select (Invitrogen) for 5 minutes at 37° C. and separated into a single cell. After being subjected to centrifugation for 2 minutes at 300 rpm, the cells were collected and suspended in TeSR2 (a medium not containing a heterogeneous animal-derived component and a serum component, STEMCELL Technologies.) containing Y-27362 ((R)-(+)-trans-N-(4-pyridyl)-4-(1-aminoethyl)-cyclohexane carboxamide.2HCl.$H_2O$, an Rho binding kinase inhibitor, Wako Pure Chemical Industries, Ltd.) at a final concentration of 10 μM.

Each of RCP-1 to RCP-11, RCP-21, RCP-25, and RCP-26 as control, human vitronectin (extracted from human serum, BD Biosciences), and recombinant laminin (rLaminin-5: Oriental Yeast Co., ltd. and Human Recombinant Laminin-511: BIOLAMINA AB) was added to and suspended in a predetermined buffer (a dialysis buffer used in <GRAVY value and aggregation characteristics> described above for RCP-1 to RCP-11, and PBS for RCP-21, RCP-25, human vitronectin, and recombinant laminin) at the concentration shown in Table 7, thereby preparing samples 1 to 17. The samples were added to the respective wells of a 96-well plate and adsorbed onto the plate by being held for 2 hours at 37° C.

Into the respective wells of the 96-well plate treated with the peptides, iPS cells were seeded at a cell density of 30,000 cells/well. After the cells were cultured for 24 hours, the nonadhesive cells were washed off with PBS, and only the adhesive cells were immobilized by using 4% (v/v) paraformaldehyde (Wako Pure Chemical Industries, Ltd.). By using an Attophos (registered trademark) AP Fluorescent Substrate System (Promega Corporation), the ALP activity was calculated, and from the calibration curve, the number of undifferentiated iPS cells having the ALP activity was calculated. The results are shown in Table 7. In Table 7, the cell adhesion rate is expressed as a ratio calculated by regarding the cell adhesion rate obtained from the sample 15 using natural vitronectin as being 100%. n=3.

TABLE 7

| | Type of peptide | Added amount | Cell adhesion rate (%) |
|---|---|---|---|
| Sample 1 | RCP-1 | 200 pmol/cm$^2$ | 109.3 ± 5.3 |
| Sample 2 | RCP-2 | 20 μg/cm$^2$ | 98.7 ± 6.2 |
| Sample 3 | RCP-3 | 20 μg/cm$^2$ | 106.1 ± 4.5 |
| Sample 4 | RCP-4 | 20 μg/cm$^2$ | 100.1 ± 4.5 |
| Sample 5 | RCP-5 | 10 μg/cm$^2$ | 94.1 ± 6.5 |
| Sample 6 | RCP-6 | 20 μg/cm$^2$ | 92.8 ± 4.4 |
| Sample 7 | RCP-7 | 5 μg/cm$^2$ | 88.6 ± 8.1 |
| Sample 8 | RCP-8 | 5 μg/cm$^2$ | 89.2 ± 1.4 |
| Sample 9 | RCP-9 | 20 μg/cm$^2$ | 95.5 ± 10.2 |
| Sample 10 | RCP-10 | 20 μg/cm$^2$ | 93.0 ± 7.8 |
| Sample 11 | RCP-11 | 5 μg/cm$^2$ | 95.9 ± 4.6 |
| Sample 12 | RCP-21 | 200 pmol/cm$^2$ | 93.5 ± 7.9 |
| Sample 13 | RCP-25 | 200 pmol/cm$^2$ | 13.2 ± 3.4 |
| Sample 14 | RCP-26 | 200 pmol/cm$^2$ | 9.4 ± 2.9 |
| Sample 15 | Natural vitronectin | 130 pmol/cm$^2$ | 100 ± 5.5 |
| Sample 16 | rLaminin-5 | 3.2 μg/cm$^2$ | 155.7 |
| Sample 17 | Laminin-511 | 5.0 μg/cm$^2$ | 142.0 |

As shown in Table 7, RCP-1 to RCP-11 and RCP-21, which included the 1$^{st}$ to 55$^{th}$ amino acids of the sequence represented by SEQ ID NO: 3, and natural human vitronectin were excellent in the cell adhesion rate of the iPS cells. Particularly, the cell adhesion rate was higher in RCP-1 to RCP-11, which did not include a portion of the 56$^{th}$ to 268$^{th}$ amino acids of the sequence represented by SEQ ID NO: 3 or included none of the above amino acids, than in the natural human vitronectin and RCP-21 having the same amino acid sequence as the natural human vitronectin. Therefore, it is understood that a sequence important for the cell adhesion is present in the 1$^{st}$ to 55$^{th}$ amino acids of the sequence represented by SEQ ID NO: 3.

<Cell Adhesiveness Evaluation 2>

The polypeptides shown in Table 8 were synthesized by an Fmoc solid-phase synthesis method. A surface onto which natural vitronectin was adsorbed at a concentration of 130 pmol/cm$^2$ was prepared, and then a cell suspension to which 100 μM of the aforementioned synthetic polypeptides were added was seeded into wells at a ratio of 30,000 cells/well. The number of adhesive cells 24 hours after seeding was calculated in the same manner as in <Cell adhesiveness evaluation 1>, and the results are shown in Table 8. In Table 8, the cell adhesion rate is expressed as a ratio calculated by regarding the cell adhesion rate obtained by using a culture solution not containing the synthetic polypeptides as being 100%. n=3.

TABLE 8

| | Sequence of synthetic peptide | Cell adhesion rate (%) | SEQ ID No |
|---|---|---|---|
| Peptide-1 | DQESCKGRCTEGFNVDKKCQ | 91.8 ± 1.2 | 32 |
| Peptide-2 | KGRCTEGFNVDKKCQCDELC | 92.7 ± 19.6 | 33 |
| Peptide-3 | EGFNVDKKCQCDELCSYYQS | 102.5 ± 4.2 | 34 |

TABLE 8-continued

| | Sequence of synthetic peptide | Cell adhesion rate (%) | SEQ ID No |
|---|---|---|---|
| Peptide-4 | DKKCQCDELCSYYQSCCTDY | 63.8 ± 11.6 | 35 |
| Peptide-5 | CCTDYTAECKPQVTRGDVFT | 70.5 ± 7.1 | 36 |
| Peptide-6 | TAECKPQVTRGDVFTMPEDE | 52.7 ± 10.3 | 37 |
| Peptide-7 | CCTDYTAECKPQVTRGEVFT | 86.7 ± 7.1 | 38 |
| Peptide-8 | TAECKPQVTRGEVFTMPEDE | 83.8 ± 14.8 | 39 |

From Table 8, it is understood that while the adhesion of cells to the natural vitronectin is significantly hindered by the addition of Peptides-4, 5, and 6 including CSYYQSC (SEQ ID NO: 1) or RGD, the adhesion of cells is not hindered by the addition of Peptides-1, 2, and 3 not including CSYYQSC (SEQ ID NO: 1) and RGD and Peptides-7 and 8 obtained by substituting the RGD sequence of Peptides-5 and 6 with RGE. Accordingly, it is understood that the polypeptide exhibits cell adhesion ability, in a case where the polypeptide includes at least one of CSYYQSC (SEQ ID NO: 1) and RGD.

<Growth Evaluation>

Figure 2:
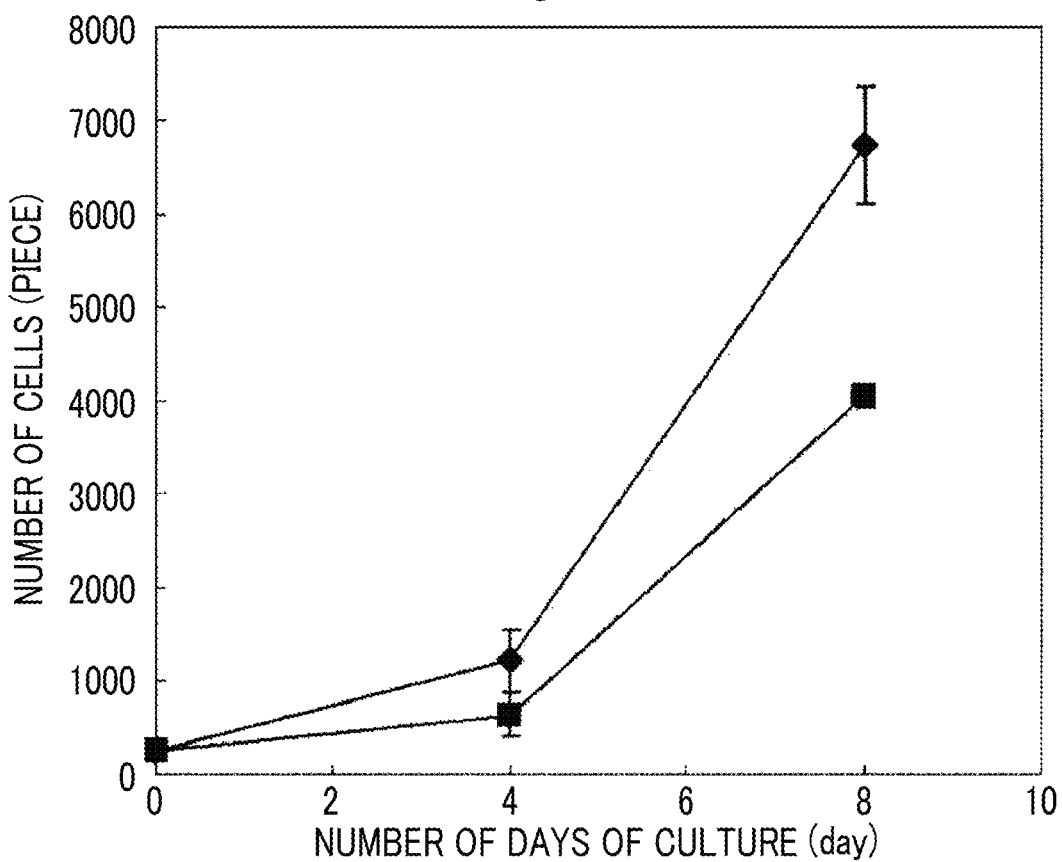
FIG. 2 is a graph showing growth curves of iPS cells using each polypeptide in the reference examples of the present invention.

The iPS cells collected in the same manner as in <Cell adhesiveness evaluation 1> were seeded into a 96-well plate, onto which RCP-1, RCP-21, and natural human vitronectin were adsorbed, at a ratio of 250 cells/well and cultured for 8 days in a 5% $CO_2$ incubator at 37° C. The number of adhesive cells after different days of culture was measured in the same manner as in <Cell adhesiveness evaluation 1>, thereby obtaining growth curves. FIG. 2 shows the growth curves. In FIG. 2, a black rhombus indicates a case using RCP-1, and a black square indicates a case using RCP-21.

By adding RCP-1 to RCP-11 and Human Recombinant Laminin-511 as control at the concentration shown in Table 9, samples 1 to 12 were prepared. The samples were seeded into a 96-well plate, onto which each of the polypeptides was adsorbed in the same manner as in <Cell adhesiveness evaluation 1>, at a ratio of 5,000 cells/well and cultured for 3 days in a $CO_2$ incubator at 37° C. The number of cells after 3 days was calculated in the same manner as in <Cell adhesiveness evaluation 1>. The results are shown in Table 9. In Table 9, the number of cells after 3 days is expressed as a ratio calculated by regarding the number of cells obtained by using the sample 1 as being 100%.

TABLE 9

| | Type of peptide | Added amount | Number of cells after 3 days (%) |
|---|---|---|---|
| Sample 1 | RCP-1 | 80 µg/cm² | 100.0 |
| Sample 2 | RCP-2 | 20 µg/cm² | 81.7 |
| Sample 3 | RCP-3 | 20 µg/cm² | 109.7 |
| Sample 4 | RCP-4 | 20 µg/cm² | 120.7 |
| Sample 5 | RCP-5 | 10 µg/cm² | 121.2 |
| Sample 6 | RCP-6 | 20 µg/cm² | 70.5 |
| Sample 7 | RCP-7 | 5 µg/cm² | 89.9 |
| Sample 8 | RCP-8 | 5 µg/cm² | 171.0 |
| Sample 9 | RCP-9 | 20 µg/cm² | 105.8 |
| Sample 10 | RCP-10 | 20 µg/cm² | 101.9 |
| Sample 11 | RCP-11 | 5 µg/cm² | 153.5 |
| Sample 12 | Laminin-511 | 1.28 µg/cm² | 56.8 |

As shown in FIG. 2, RCP-1 showed higher cell growth properties compared to RCP-21 having the amino acid sequence of the natural vitronectin, and on Day 8 of culture, the number of cells in the case where the RCP-21 was used was about ⅓ of the number of cells in the case where the RCP-1 was used. From the increase and decrease in the obtained number of cells, the doubling time was calculated. As a result, it was confirmed that it takes 46.4±2.1 hours for the number of cells to be doubled in a case where RCP-1 is used, and 67.7±2.1 hours in a case where RCP-21 is used.

From Table 9, it is understood that all of RCP-1 to RCP-11 show a higher cell growth rate compared to laminin which is the extracellular matrix just like vitronectin. Furthermore, it is understood that even if the 274th cysteine residue in SEQ ID NO: 3 was substituted with a serine residue, the same high cell growth rate as described above is obtained.

From the results shown in FIG. 2 and Table 9, it is understood that surprisingly, RCP-1 to RCP-11, which include a sequence effective for the cell growth and the adsorption onto the cell culture surface but do not include a sequence corresponding to a portion or the entirety of the 56th to 268th amino acids of natural human vitronectin, have a growth ability higher than that of RCP-21 having the same sequence as the human vitronectin and Laminin-511 as a comparative example. Furthermore, from Table 9, it is understood that all of RCP-1 to RCP-11 including both the sequences of CSYYQSC (SEQ ID NO: 1) and RDG and the sequence of PRPSLAKKQRFRHRNRKGYRSQRGHSR-GRNQN (SEQ ID NO: 2) show high cell growth properties.

Furthermore, from Table 9, it is understood that all of RCP-1 to RCP-11 including both the sequences of CSYYQSC and RDG and the sequence of PRPSLAKKQR-FRHRNRKGYRSQRGHSRGRNQN show high cell growth properties.

<Cell Adhesiveness Evaluation 3>

The cell adhesiveness was evaluated in the same manner as in <Cell adhesiveness evaluation 1>, except that RCP-1 was used after the concentration thereof was adjusted to 125 pmol/cm² to 1,000 pmol/cm² by using PBS. The results are shown in Table 10. In Table 10, the cell adhesion rate is expressed as a ratio calculated by regarding a cell adhesion rate with respect to the cell culture surface, onto which natural vitronectin is adsorbed at a concentration of 130 pmol/cm², as being 100%. n=3.

TABLE 10

| Type of peptide | Added amount | Cell adhesion rate (%) |
|---|---|---|
| RCP-1 | 1000 pmol/cm² | 98.5 ± 17.2 |
| RCP-1 | 500 pmol/cm² | 108.8 ± 23.0 |
| RCP-1 | 250 pmol/cm² | 89.2 ± 10.6 |
| RCP-1 | 125 pmol/cm² | 90.3 ± 25.3 |
| Natural vitronectin | 130 pmol/cm² | 100 ± 5.5 |

As shown in Table 10, in a case where the amount of RCP-1 added (applied) was equal to or greater than 125 pmol/cm², the adhesiveness of iPS cells with respect to RCP-1 was equivalent to the cell adhesion rate of the natural vitronection.

<Evaluation of Maintenance of Undifferentiated State> iPS cells collected in the same manner as in <Cell adhesiveness evaluation 1> were suspended in TeSR2. The iPS cells were seeded into 6-well plate (Tissue culture-treated, Falcon), onto which each of the samples 1, 2, 5, 6, and 7 used in <Cell adhesiveness evaluation 1> was adsorbed in the same manner as in <Cell adhesiveness evaluation 1>, and cultured in a $CO_2$ incubator at 37° C. Except for the day after the seeding, the medium was replaced every day. In the same method as described above, the cells were subcultured every six days. FIGS. 3A to 3E shows forms of the iPS cells cultured on each of the samples.

After being cultured for 1 month under the conditions described above, the cells were immobilized using 4% paraformaldehyde and treated with 1% Triton-X/PBS so as to enhance the membrane permeability. After the cells were subjected to a blocking treatment using an Image IT Signal Enhancer (Invitrogen), an anti-human NANOG antibody (AF 1997, R&D Systems, Inc.), an Alexa Fluor 555 binding rabbit anti-goat IgG antibody (Invitrogen), and DAPI (4',6-diamidino-2-phenylindole, Dojindo Molecular Technologies, Inc.) were added thereto for labeling, and the cells were imaged using a fluorescence microscope. FIGS. 4A to 4E shows the fluorescence microscopic images.

Figure 3A:
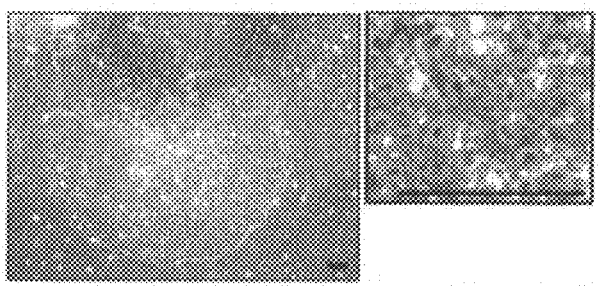
FIG. 3A shows a morphic image (left side) and a magnified image (right side) of an iPS cell colony cultured on each polypeptide in the reference examples of the present invention.
Figure 3B:
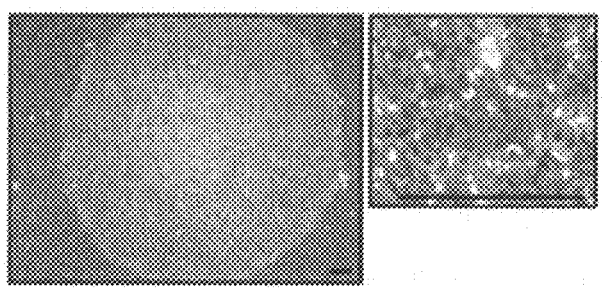
FIG. 3B shows a morphic image (left side) and a magnified image (right side) of an iPS cell colony cultured on each polypeptide in the reference examples of the present invention.
Figure 3C:
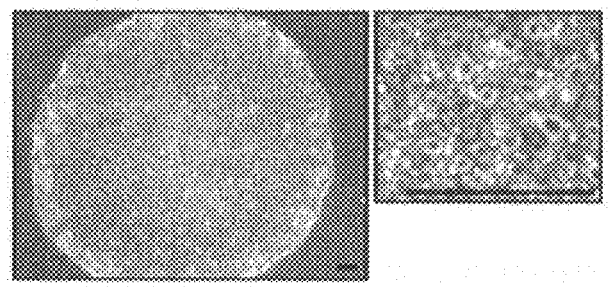
FIG. 3C shows a morphic image (left side) and a magnified image (right side) of an iPS cell colony cultured on each polypeptide in the reference examples of the present invention.
Figure 3D:
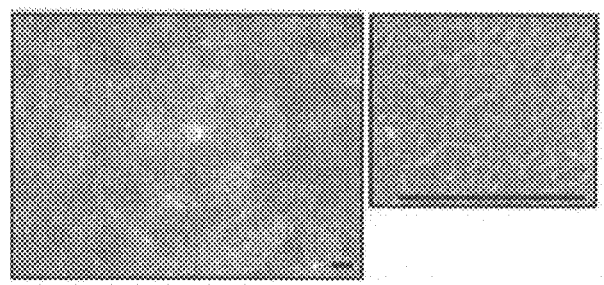
FIG. 3D shows a morphic image (left side) and a magnified image (right side) of an iPS cell colony cultured on each polypeptide in the reference examples of the present invention.
Figure 3E:
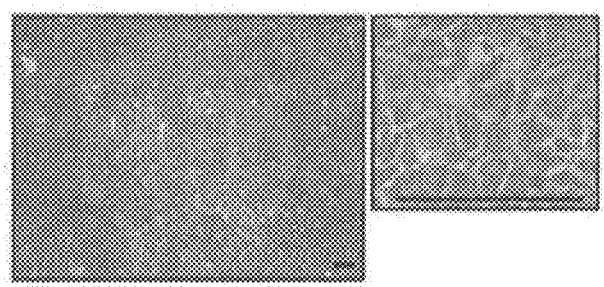
FIG. 3E shows a morphic image (left side) and a magnified image (right side) of an iPS cell colony cultured on each polypeptide in the reference examples of the present invention.
Figure 4A:
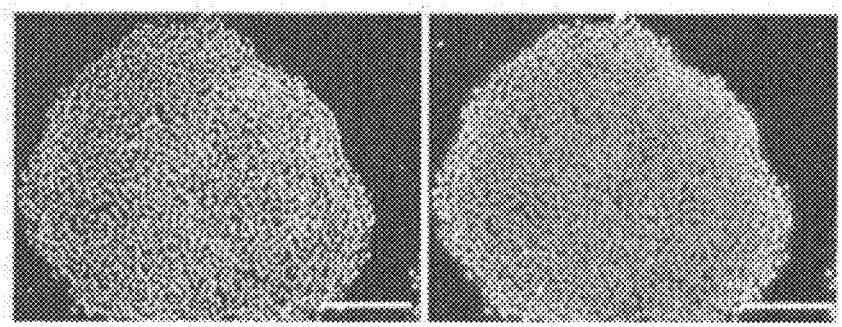
FIG. 4A shows an image of iPS cells stained with DAPI (left side) and an image of iPS cells stained with NANOG (right side) that are captured in a case where the iPS cells are cultured on each polypeptide in the reference examples of the present invention.
Figure 4B:
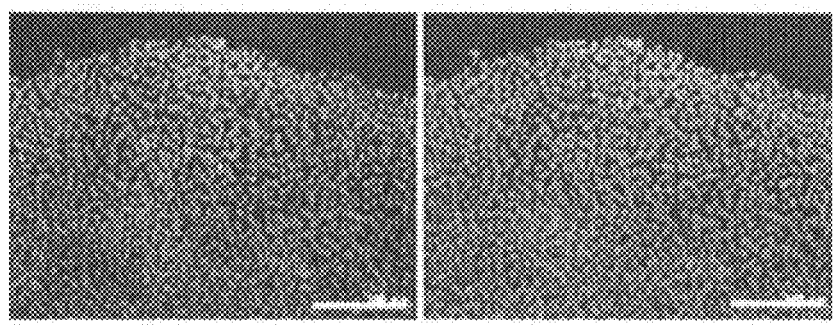
FIG. 4B shows an image of iPS cells stained with DAPI (left side) and an image of iPS cells stained with NANOG (right side) that are captured in a case where the iPS cells are cultured on each polypeptide in the reference examples of the present invention.
Figure 4C:
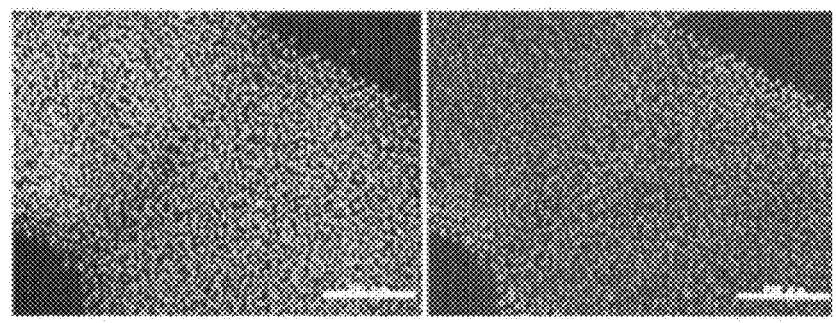
FIG. 4C shows an image of iPS cells stained with DAPI (left side) and an image of iPS cells stained with NANOG (right side) that are captured in a case where the iPS cells are cultured on each polypeptide in the reference examples of the present invention.
Figure 4D:
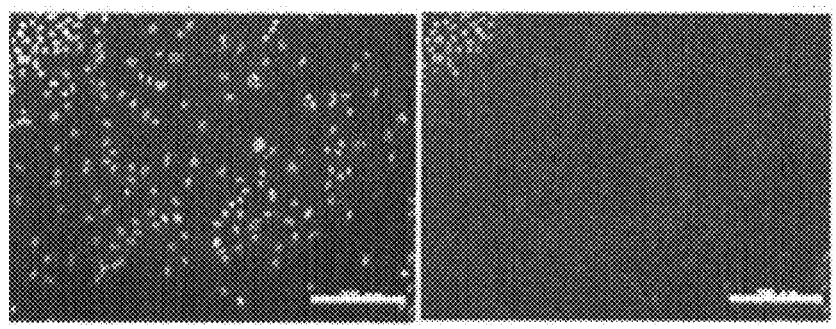
FIG. 4D shows an image of iPS cells stained with DAPI (left side) and an image of iPS cells stained with NANOG (right side) that are captured in a case where the iPS cells are cultured on each polypeptide in the reference examples of the present invention.
Figure 4E:
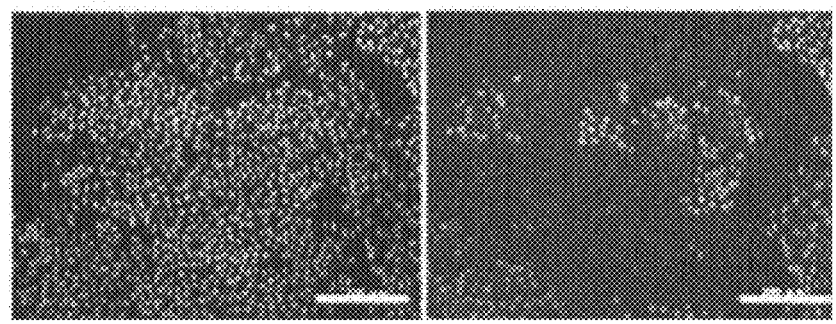
FIG. 4E shows an image of iPS cells stained with DAPI (left side) and an image of iPS cells stained with NANOG (right side) that are captured in a case where the iPS cells are cultured on each polypeptide in the reference examples of the present invention.

FIGS. 3A and 4A show the iPS cells cultured on RCP-1; FIGS. 3B and 4B show the iPS cells cultured on RCP-11; FIGS. 3C and 4C show the iPS cells cultured on natural human vitronectin; FIGS. 3D and 4D show the iPS cells cultured on rLaminin-5; and FIGS. 3E and 4E show the iPS cells cultured on rLaminin-511. The scale bar in the images indicates 100 μm. In FIGS. 3A to 3E, the images on the left side are full images of the colony, and the images on the right side are magnified images. In FIGS. 4A to 4E, the images on the left side are images of the cells stained with DAPI, and the images on the right side are images of the cells stained with an anti-NANOG antibody. The scale bar in FIGS. 3A to 4E indicates 200 μm.

As shown in FIGS. 3A to 3E, the iPS cells, which were cultured on RCP-1, RCP-21, and the natural human vitronectin including a sequence effective for the cell growth and the adsorption onto the cell culture surface, had a form specific to undifferentiated cells which have a homogeneous colony and posses nuclei at a high ratio. Furthermore, as shown in FIGS. 4A to 4E, the iPS cells, which were cultured on RCP-1, RCP-21, and the natural human vitronectin having a cell growth domain and an adsorption domain, strongly expressed NANOG in the entirety of the colony, and accordingly, it was understood that the undifferentiated state is excellently maintained.

From the results of the above evaluation, it was understood that the polypeptide, which includes one of the sequences of CSYYQSC (SEQ ID NO: 1) and RGD and the sequence of PRPSLAKKQRFRHRNRKGYRSQRGHSR-GRNQN (SEQ ID NO: 2) and consists of 40 to 450 amino acid residues, is excellent in the adsorbability with respect to the cell culture surface. Furthermore, it was understood that under the condition of co-culture with iPS cells, such a polypeptide is equivalent to RCP-11 having a sequence equivalent to that of the natural vitronectin and human vitronection, in terms of the cell adhesiveness of the iPS cell and the maintenance of the undifferentiated state, and is better than RCP-21 in terms of the growth properties of the iPS cells. It was also understood that all of RCP-1 to RCP-11 are excellent in terms of the cell adhesiveness of the iPS cells and the maintenance of the undifferentiated state. Such excellent results in terms of the aforementioned abilities were not obtained from other polypeptides or the recombinant laminin as control.

Example 1

Among RCP-1 to RCP-11 obtained as above, RCP-11 and RCP-5 were used in the following examples.

The polypeptide of RCP-11 was subjected to electrophoresis just like RCP-1 or the like by using Ready Gel (12.5%, Bio-Rad Laboratories, Inc.) and stained with a GelCode™ Blue Stain Reagent (Thermo Scientific). As a result, a single band was confirmed at a site corresponding to a molecular weight of 16.3 kDa expected from the amino acid sequence. For RCP-5, a single band was also confirmed at a site corresponding to a molecular weight of 14.6 kDa expected from the amino acid sequence.

Furthermore, for evaluation, human iPS cells ("Tic") that were retention-cultured as described in <Cell adhesiveness evaluation 1> of reference example were treated with TrypLE Select (Invitrogen) for 5 minutes at 37° C. and separated into a single cell. After being subjected to centrifugation for 2 minutes at 300 rpm, the cells were collected, suspended in each medium, and used for the evaluation in each example. Herein, Y-27362 ((R)-(+)-trans-N-(4-pyridyl)-4-(1-aminoethyl)-cyclohexane carboxamide.2HCl.H$_2$O, an Rho binding kinase inhibitor, Wako Pure Chemical Industries, Ltd.) was added to all of the media at a final concentration of 10 μM.

<Cell Growth Property Evaluation 1>

Each of RCP-11, RCP-5, and recombinant laminin (Human Recombinant Laminin-511: BIOLAMINA AB) as control was added to and suspended in a predetermined buffer (a dialysis buffer used in <GRAVY value and aggregation characteristics> of reference examples for RCP-11 and RCP-5, and PBS for the recombinant laminin) at the final concentration shown in Table 11, thereby preparing polypeptide solutions. The polypeptide solutions were added to the respective wells of a plasma-treated 96-well plate made of polystyrene (BD Falcon) having a plasma-treated cell culture surface and held as they were so as to be adsorbed onto the plate for 2 hours at 37° C. In this way, a peptide-treated 96-well plate having a polypeptide-coated surface was obtained. The iPS cells suspended in the respective media shown in Table 11 were seeded into the respective wells of the obtained peptide-treated 96-well plate at a cell density of 10,000 cells/well. After the cells were cultured for 72 hours, nonadhesive cells were washed off with PBS, and only adhesive cells were immobilized using 4% by mass of paraformaldehyde (Wako Pure Chemical Industries, Ltd.). By using an Attophos (registered trademark) AP Fluorescent Substrate System (Promega Corporation), the ALP activity was calculated, and from the calibration curve, the number of undifferentiated iPS cells having the ALP activity was calculated. The results are shown in Table 11. In Table 11, the cell adhesion rate is expressed as a ratio calculated by regarding the number of pluripotent stem cells after the culture for 72 hours in a combination of RCP-11 and Essential 8 as being 100%. n=3.

Herein, as the media in the table, the following commercial products were used.

Essential 8 (Life Technologies, hereinafter, abbreviated to "E8" in some cases)

NutriStem (Biological Industries, Ltd.)

TeSR2 (trade name, STEMCELL Technologies, Inc.)

ReproFF2 (trade name, Reprocell Inc.)

StemPro hESC SFM (trade name, Life Technologies, hereinafter, described as "Stempro" in some cases)

In Table 11, "% by mass" in the concentration of 2-mercaptoethanol is a proportion (w/v %) of mass (g) of 2-mercaptoethanol per 100 mL of the total volume of the medium at the time of culture.

TABLE 11

| Medium | 2-Mercaoto-ethanol concentration | Cell growth rate | | |
|---|---|---|---|---|
| | | RCP-11 (100 μg/ml) | RCP-5 (100 μg/ml) | Recombinant laminin (20 μg/ml) |
| Essential8 | 0 | 100 | 84.4 | 45.9 |
| NutriStem | 0 | 129.1 | 123 | 98.8 |
| TeSR2 | 48.6 μM (0.00038% by mass) | 71.8 | 54.4 | 14.4 |
| ReproFF2 | 102.4 μM (0.0008% by mass) | 84.7 | 70.3 | 93.9 |
| StemPro hESC SFM | 100 μM (0.00078% by mass) | 13.6 | 20.1 | 103.7 |

As shown in Table 11, in a case where the cells were cultured on the cell culture surface, onto which RCP-11 and RCP-5 were adsorbed, by using Essential 8 or NutriStem not containing 2-mercaptoethanol, the cell growth properties of the cell culture surface were better than in a case where the cells were cultured using other media containing 2-mercaptoethanol. In contrast, on the cell culture surface onto which the recombinant laminin was adsorbed, a clear correlation could not be confirmed between the presence or absence of 2-mercaptoethanol and the cell growth properties.

Example 2

Cell Growth Property Evaluation 2

A cell culture surface coated with RCP-11 was prepared in the same manner as in <Cell growth property evaluation 1> of Example 1. iPS cells collected in the same manner as in <Cell growth property evaluation 1> were suspended in the respective media composed as shown in Table 12 and seeded into wells at a cell density of 10,000 cells/well. After the cells were cultured for 72 hours, the number of cells were quantified in the same manner as in <Cell growth property evaluation 1>, and the cell growth properties were evaluated based on a cell growth rate which is a ratio calculated by regarding the number of cells cultured using RPC-11 as being 100%. The results are shown in Table 12.

TABLE 12

| Medium | 2-Mercaptoethanol concentration | Cell growth rate | |
|---|---|---|---|
| | | RCP-11 (100 μg/ml) | Recombinant laminin (20 μg/ml) |
| Essential8 | 0 | 100 | 45.9 |
| | 10 μM (0.0000078% by mass) | 104.1 | 48.6 |
| | 10 μM (0.000078% by mass) | 97.3 | 48.1 |
| | 100 μM (0.00078% by mass) | 49.2 | 44.6 |
| | 1 mM (0.0078% by mass) | 38.7 | 40.9 |
| | 10 mM (0.078% by mass) | 40.2 | 39.3 |

From Table 12, it is understood that the cell growth properties of the cell culture surface tend to decrease depending on the concentration of 2-mercaptoethanol. In a case where the cells were cultured on the cell culture surface coated with the recombinant laminin, such characteristics were not observed.

Example 3

Evaluation 1 about Amount of Residual Polypeptide Adsorbed

Figure 5:
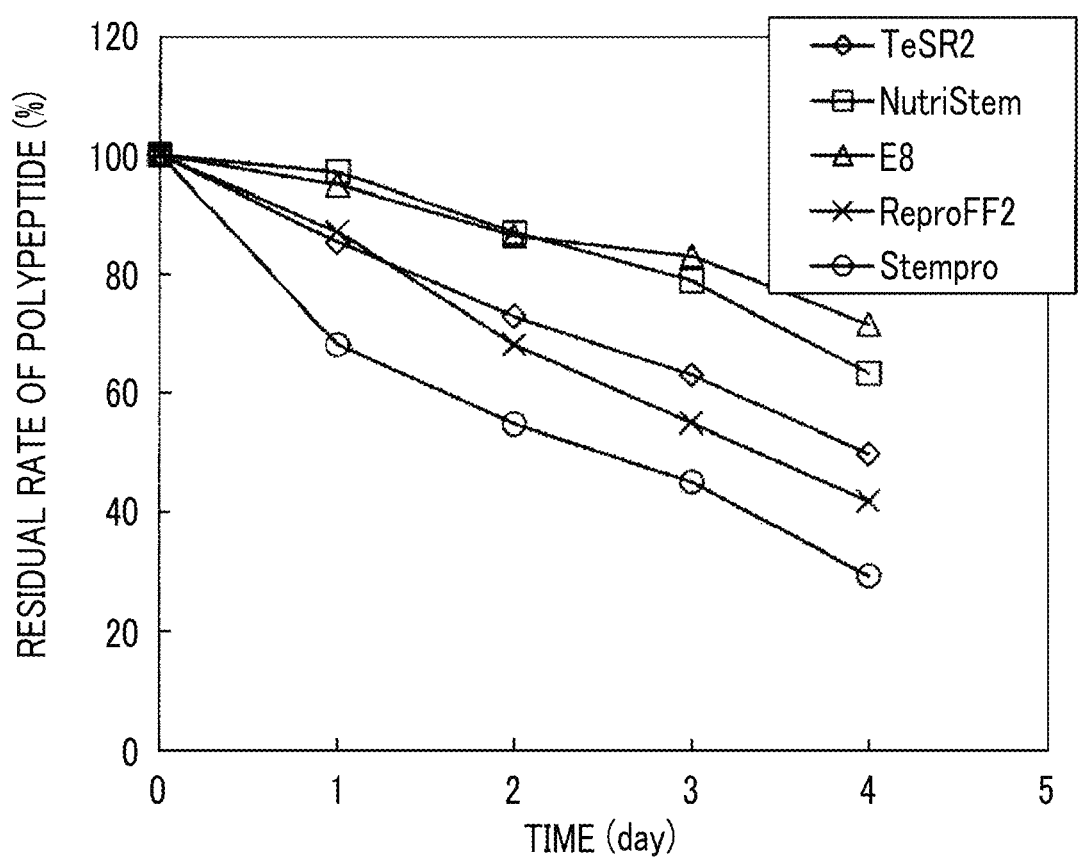
FIG. 5 is a graph showing the results of evaluation of the amount of residual polypeptides adsorbed onto a cell culture surface coated with RPC-11 in a case where iPS cells are cultured on the cell culture surface in Example 3 of the present invention by using each medium.
Figure 6:
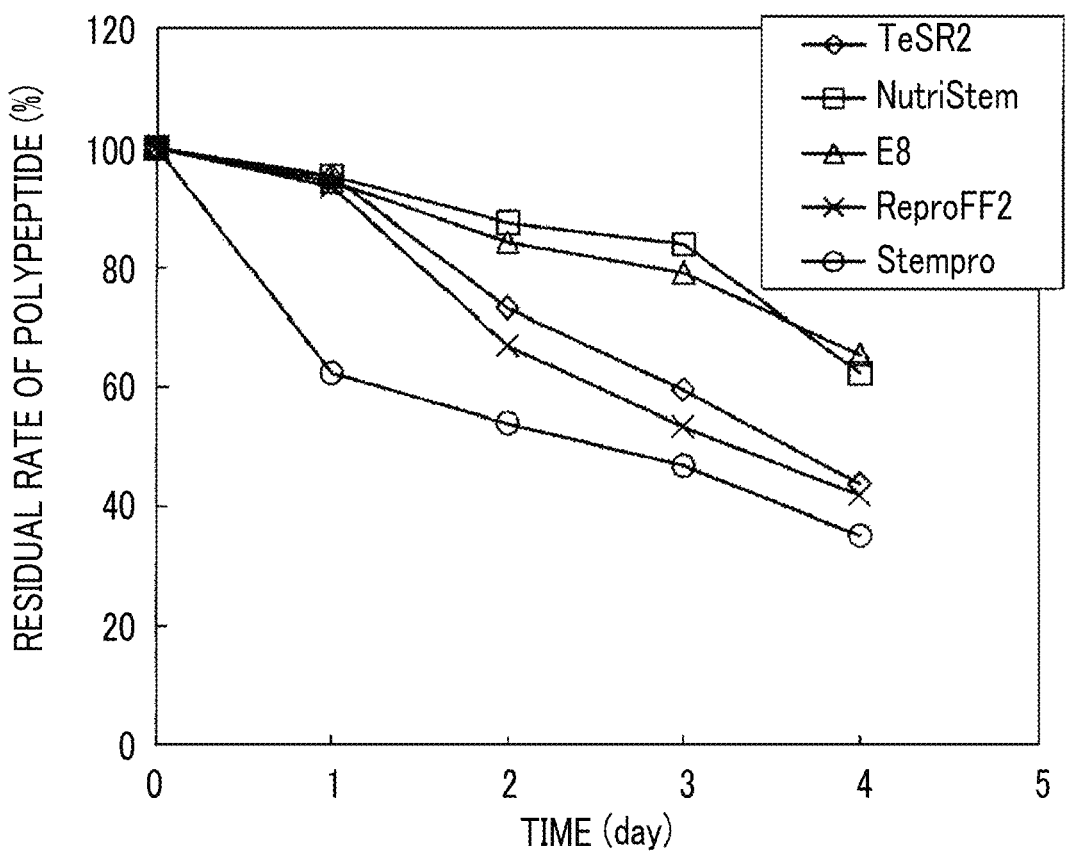
FIG. 6 is a graph showing the results of evaluation of the amount of residual polypeptides adsorbed onto a cell culture surface coated with RPC-5 in a case where iPS cells are cultured on the cell culture surface in Example 3 of the present invention by using each medium.

RCP-11 and RCP-5 were prepared by using a predetermined buffer (the dialysis buffer used in <GRAVY value and aggregation characteristics> of reference examples) such that their concentration became 100 μg/ml. The polypeptides were added to the respective wells of a plasma-treated 96-well plate made of polystyrene having a plasma-treated cell culture surface and held as they were for 2 hours at 37° C. so as to be adsorbed onto the plate, thereby obtaining a polypeptide-coated surface. After the wells were washed with PBS, the respective media were added thereto, followed by incubation at 37° C. for a predetermined time. The wells were washed with PBS, and then 20% by mass of an immunoblocking solution (DS Pharma Biomedical Co., Ltd.) was added thereto, followed by incubation for 30 minutes at 37° C., thereby performing a blocking treatment. After the wells were washed with PBS-T (PBS containing 0.05% by mass of Tween-20), 5% by mass of an immunoblocking solution (DS Pharma Biomedical Co., Ltd.) containing an anti-human vitronectin antibody (Thermo Fisher Scientific Inc.) was added thereto, followed by incubation for 2 hours at room temperature. After the wells were washed with PBS-T, a 5% by mass of immunoblocking solution (DS Pharma Biomedical Co., Ltd.) containing an HRP-labeled anti-IgG antibody (Thermo Fisher Scientific Inc.) was added thereto, followed by incubation for 1 hour at room temperature. After the wells were washed with PBS-T, a TMB Substrate (Wako Pure Chemical Industries, Ltd.) was added thereto for developing color, and then 1 N hydrochloric acid was added thereto to stop the color reaction. By using a plate reader, the absorbance was measured, and the amount of the residual RCP-11 and RCP-5 was determined (absorption wavelength: 450 nm, control wavelength: 650 nm). FIG. 5 shows the results obtained from the case where RCP-11 is used, and FIG. 6 shows the results obtained from the case where RCP-5 is used.

Table 13 shows the residual rate of RCP-11 and RCP-5 four days after the starting of culture. In Table 13, the residual rate of RCP-11 and RCP-5 is expressed as a ratio (%) calculated by regarding the amount of the polypeptides adsorbed immediately after the starting of culture as being 100.

TABLE 13

| | Residual rate of polypeptide (%) | | | | |
|---|---|---|---|---|---|
| | Essential8 | NutriStem | TeSR2 | ReproFF2 | Stempro hESC SFM |
| RCP-11 | 71.8 | 63.5 | 49.9 | 42.0 | 29.4 |
| RCP-5 | 65.6 | 62.5 | 44.0 | 42.1 | 35.3 |

From FIGS. 5 and 6 and Table 13, it is understood that the residual rate of adsorbed RCP-11 and RCP-5 decreases further with the passage of time in the case where the cells were cultured in a medium not containing 2-mercaptoethanol than in the case where the cells were cultured in a medium containing 2-mercaptoethanol.

Example 4

Evaluation 2 about Amount of Residual Polypeptide Adsorbed

Figure 7:
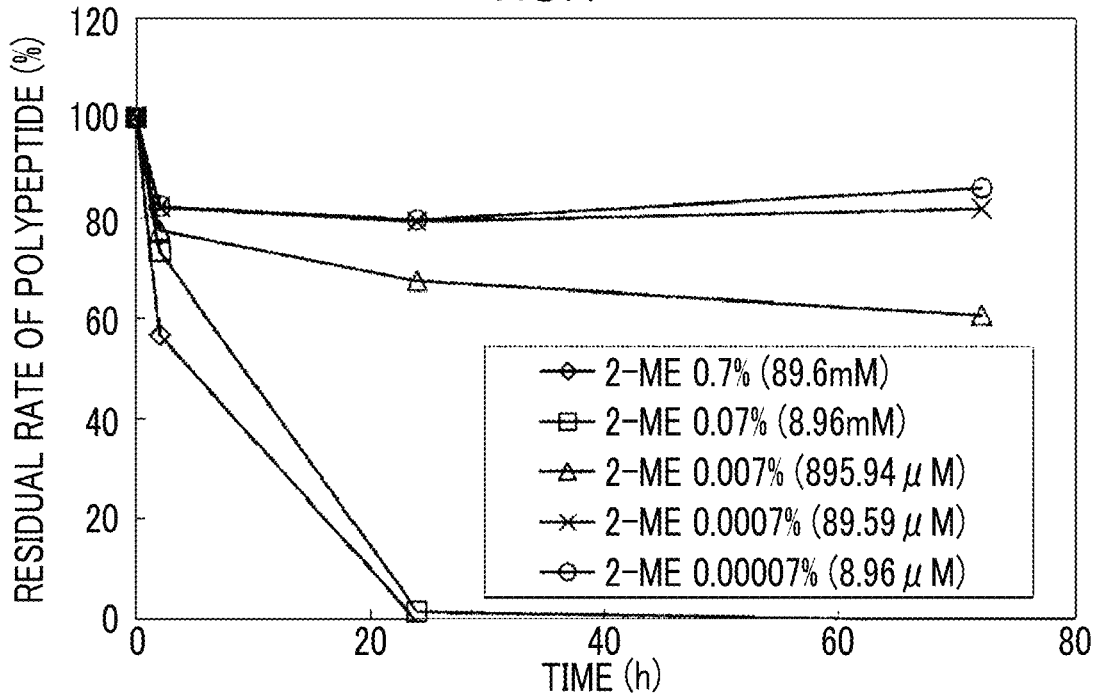
FIG. 7 is a graph showing the results of evaluation of the amount of residual polypeptides adsorbed onto a cell culture surface coated with RCP-11 in a case where iPS cells are cultured on the cell culture surface in Example 4 of the present invention by using media containing 2-mercaptoethanol at different concentrations.

A cell culture surface coated with RCP-11 was prepared in the same manner as in Example 3, and then PBS containing 2-mercaptoethanol was added thereto such that the final concentration of 2-mercaptoethanol became 89.6 mM (0.7% by mass), 8.96 mM (0.07% by mass), 895.94 μM (0.007% by mass), 89.59 μM (0.0007% by mass), or 8.96 μM (0.00007% by mass), followed by incubation at 37° C. for a predetermined time. Thereafter, in the same manner as in Example 3, the amount of RCP-11 adsorbed was determined, and the residual rate of the polypeptide adsorbed was obtained. The results are shown in FIG. 7. In FIG. 7, the amount of residual RCP-11 adsorbed is expressed as a ratio calculated by regarding the amount of RCP-11 adsorbed immediately after the starting of incubation as being 100%. Furthermore, "2-ME" indicates 2-mercaptoethanol.

From FIG. 7, it is understood that the amount of residual RCP-11 tends to decrease as the concentration of 2-mercaptoethanol increases, and this shows that 2-mercaptoethanol accelerates the desorption of RCP-11.

Example 5

Relationship Between Amount of Residual Polypeptide Adsorbed and Cell Growth Properties In the same manner as in Evaluation 1 about amount of residual polypeptide adsorbed> of Example 3, RCP-11 was added to the respective wells, thereby obtaining a coated cell culture surface. Thereafter, a 2-mercaptoethanol/PBS solution of which the concentration was adjusted in advance as shown in Table 14 was added thereto, followed by incubation for 24 hours, thereby accelerating the desorption of RCP-11.

Meanwhile, in the same manner as in <Cell growth property evaluation 1> of Example 3, iPS cells were collected and suspended in Essential 8. The iPS cells were then seeded into the respective wells, to which 2-mercaptoethanol was added so as to accelerate the desorption of RCP-11, at a cell density of 10,000 cells/well, thereby starting culture.

After the cells were cultured for 72 hours, the number of cells was quantified in the same manner as in <Cell growth property evaluation 1> of Example 3. The results are shown in Table 14. In the table, each of the residual rate of RCP-11 adsorbed and the cell growth rate is expressed as a ratio calculated by regarding the residual rate of the polypeptide adsorbed and the cell growth rate in the case where the pretreatment with PBS is performed as being 100%.

TABLE 14

| Pretreatment condition | Residual rate of RCP-11 adsorbed (%) | Cell growth rate (%) |
|---|---|---|
| 2-Mercaptoethanol 89.6 mM (0.7% by mass) | 56.6 | 38.0 |
| 2-Mercaptoethanol 895.94 μM (0.007% by mass) | 77.4 | 70.7 |
| 2-Mercaptoethanol 8.96 μM (0.00007% by mass) | 82.2 | 85.2 |
| PBS | 100 | 100 |

From Table 14, it is understood that a correlation is established between the residual rate of RCP-11 adsorbed and the cell growth rate due to the pretreatment with 2-mercaptoethanol. From this fact, it is understood that due to the adsorption or desorption of RCP-11 caused by 2-mercaptoethanol, the cell growth properties of the cell culture surface deteriorate.

Example 6

Evaluation of Undifferentiated State Maintainability iPS cells were seeded onto cell culture surfaces coated with RCP-11 and RCP-5 and cultured in Essential 8. Every five to seven days after seeding, cell culture surfaces coated with RCP-11 and RCP-5 were newly prepared. The iPS cells were treated with TryPLE Select, separated into a single cell, and then collected. Thereafter, the iPS cells were subcultured by being seeded onto the newly prepared cell culture surfaces coated with RCP-11 and RCP-5. Under the conditions described above, the cells were cultured for 10 passages. FIGS. 8A to 8D shows the form of the cells after 10 passages.

The iPS cells cultured for 10 passages on the RCP-11-coated surface were immobilized using 4 v/v % paraformaldehyde, and the membrane permeability was enhanced by using 1% by mass of Triton-X/PBS. After the cells were subjected to a blocking treatment using an Image IT Signal Enhancer (Invitrogen), an anti-NANOG antibody (AF 1997, R&D Systems, Inc.), an anti-OCT 3/4 antibody, an anti-SSEA-3 antibody, an anti-S SEA-4 antibody, a anti-Tra-1-60 antibody, and an anti-Tra-1-81 antibody (Stemcell Technologies Inc), an Alexa Fluor 555 binding rabbit anti-goat IgG antibody (Invitrogen), an FITC binding goat anti-mouse IgM antibody (Stemcell Technologies Inc), and DAPI (Dojindo Molecular Technologies, Inc.) were added thereto for labeling, and the cells were imaged using a fluorescence microscope. FIGS. 9A to 9F shows the fluorescence microscopic images.

Figure 8A:
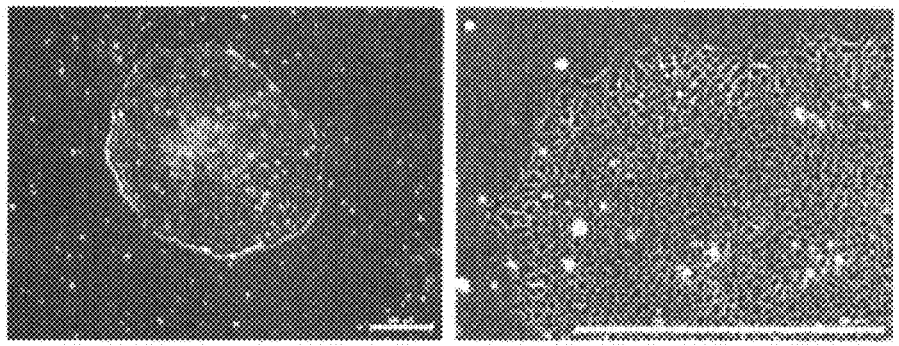
FIG. 8A shows a morphic image (left side) and a magnified image (right side) of an iPS cell colony cultured on each polypeptide in Example 6 of the present invention.
Figure 8B:
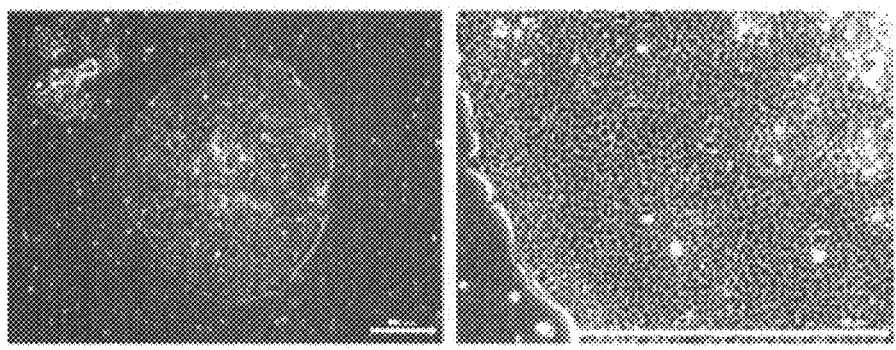
FIG. 8B shows a morphic image (left side) and a magnified image (right side) of an iPS cell colony cultured on each polypeptide in Example 6 of the present invention.
Figure 8C:
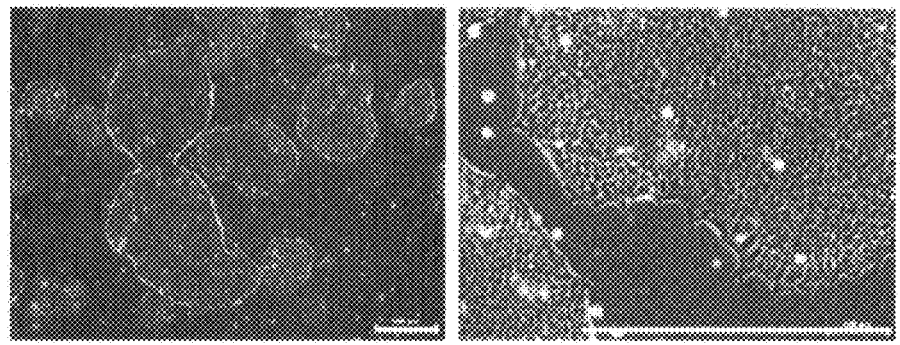
FIG. 8C shows a morphic image (left side) and a magnified image (right side) of iPS cell colony cultured on each polypeptide in Example 6 of the present invention.
Figure 8D:
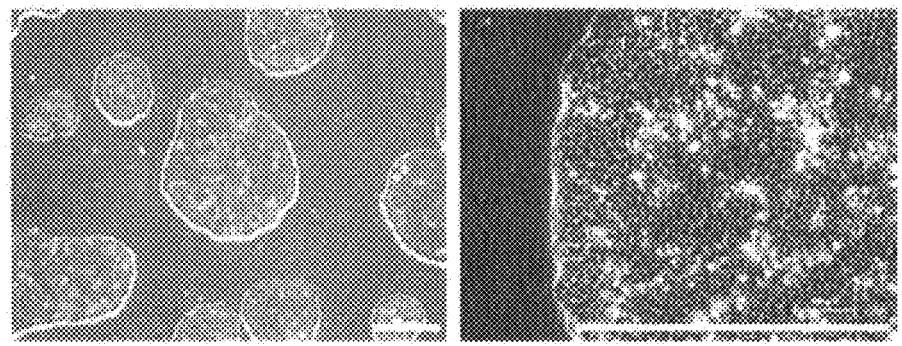
FIG. 8D shows a morphic image (left side) and a magnified image (right side) of iPS cell colony cultured on each polypeptide in Example 6 of the present invention.

FIG. 8A shows iPS cells cultured on the RCP-11-coated cell culture surface by using Essential 8; FIG. 8B shows iPS cells cultured on the RCP-5-coated surface by using Essential 8; FIG. 8C shows iPS cells cultured on the RCP-11-coated surface by using NutriStem; and FIG. 8D shows iPS cells cultured on the RCP-5-coated surface by using NutriStem. In FIGS. 8A to 8D, the images on the left side are full images of the colony, and the images on the right side are magnified images. The scale bar in FIGS. 8A to 8D indicates 500 μm.

Figure 9A:
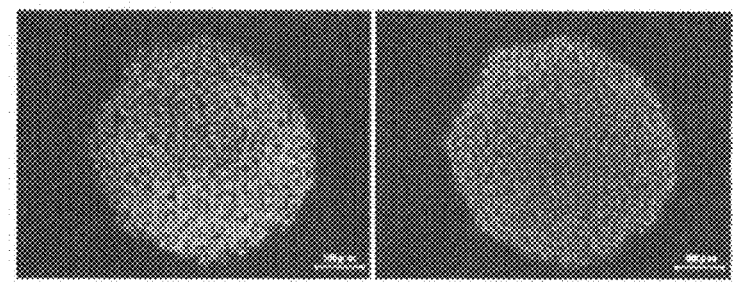
FIG. 9A shows an image of iPS cells stained with DAPI (left side) and an image of iPS cells stained with NANOG (right side) that are captured in a case where the iPS cells are cultured on each polypeptide in Example 6 of the present invention.
Figure 9B:
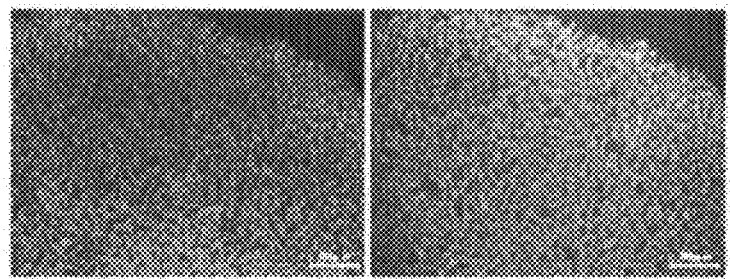
FIG. 9B shows an image of iPS cells stained with DAPI (left side) and an image of iPS cells stained with OCT 3/4 (right side) that are captured in a case where the iPS cells are cultured on each polypeptide in Example 6 of the present invention.
Figure 9C:
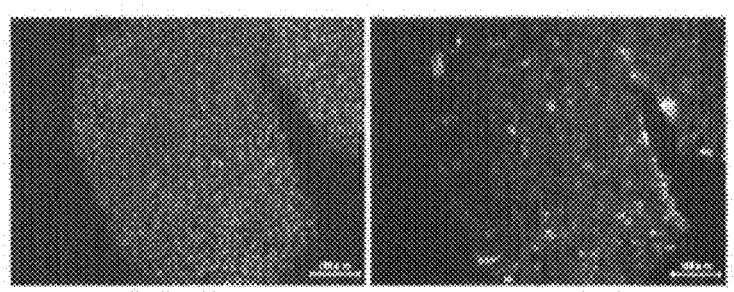
FIG. 9C shows an image of iPS cells stained with DAPI (left side) and an image of iPS cells stained with SSEA-3 (right side) that are captured in a case where the iPS cells are cultured on each polypeptide in Example 6 of the present invention.
Figure 9D:
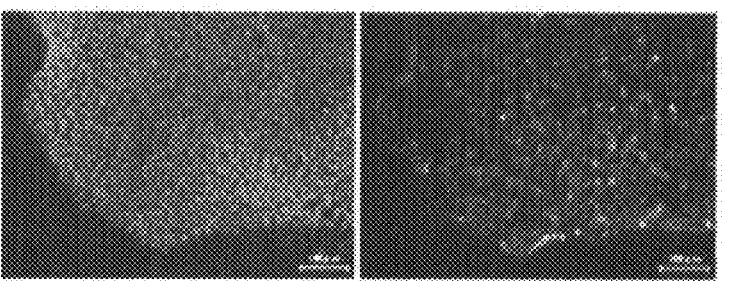
FIG. 9D shows an image of iPS cells stained with DAPI (left side) and an image of iPS cells stained with SSEA-4 (right side) that are captured in a case where the iPS cells are cultured on each polypeptide in Example 6 of the present invention.
Figure 9E:
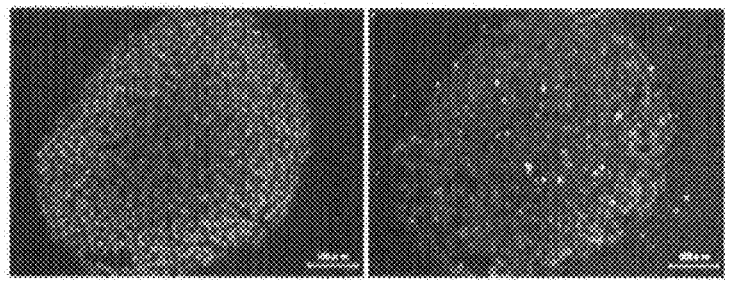
FIG. 9E shows an image of iPS cells stained with DAPI (left side) and an image of iPS cells stained with Tra-1-60 (right side) that are captured in a case where the iPS cells are cultured on each polypeptide in Example 6 of the present invention.
Figure 9F:
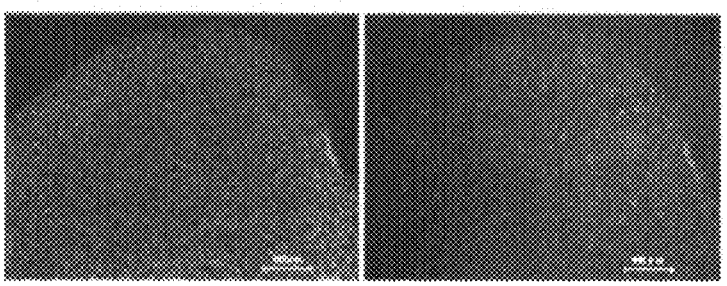
FIG. 9F shows an image of iPS cells stained with DAPI (left side) and an image of iPS cells stained with Tra-1-81 (right side) that are captured in a case where the iPS cells are cultured on each polypeptide in Example 6 of the present invention.

In FIGS. 9A to 9F, each of the images of stained cells is an image of stained iPS cells cultured on the RCP-11-coated surface by using Essential 8. The images on the left side are images of the cells stained with DAPI, and the images on the right side are images of the cells stained with NANOG (FIG. 9A), OCT 3/4 (FIG. 9B), SSEA-3 (FIG. 9C), SSEA-4 (FIG. 9D), Tra-1-60 (FIG. 9E), and Tra-1-81 (FIG. 9F). The scale bar in FIGS. 9A to 9F indicates 100 μM.

As shown in FIGS. 8A to 8D, the iPS cells, which were cultured on the cell culture surfaces coated with RCP-11 and RCP-5 by using Essential 8 and NutriStem not containing 2-mercaptoethanol, had a shape specific to undifferentiated cells which have a homogeneous colony and possess nuclei at a high ratio. Furthermore, as shown in FIGS. 9A to 9F, the iPS cells, which were cultured on the RCP-11-coated cell culture surface by using Essential 8, expressed NANOG, OCT 3/4, SSEA-3, SSEA-4, Tra-1-60, and Tra-1-81 which are markers specific to undifferentiated cells, and accordingly, it was confirmed that the undifferentiated state can be maintained.

From the evaluation results of Examples 1 to 6, it is understood that if the iPS cells are cultured on the cell culture surfaces coated with RCP-11 and RCP-5 in combination with a medium in which the content of 2-mercaptoethanol is equal to or less than 10 the pluripotent stem cells exhibit excellent growth properties, and the undifferentiated state thereof can be excellently maintained. It is also understood that, in contrast, in a case where the iPS cells are cultured in a medium containing 2-mercatoethanol at a concentration of greater than 10 μM, the growth activity of the pluripotent stem cells decreases. The evaluation results of Examples 1 to 6 clearly show that the cause of the decrease in the growth activity of the pluripotent stem cells is the desorption of RCP adsorbed onto the cell culture surface of the support that is accelerated by 2-mercaptoethanol contained in the medium at a concentration of greater than 10 μM.

Therefore, according to the present invention, a culture method for pluripotent stem cells is provided which can keep pluripotent stem cells undifferentiated and can induce high growth activity for the pluripotent stem cells.

The entirety of the disclosure of JP2013-187440 filed on Sep. 10, 2013 is incorporated into the present specification by reference.

All of the documents, patent applications, and technical standards described in the present specification are incorporated into the present specification by reference as if each of the documents, patent applications, and technical standards is specifically and independently described so as to be incorporated into the present specification by reference.

What is claimed is:

1. A culture method for pluripotent stem cells comprising:
   (a) applying a polypeptide to a cell surface of a support to obtain a polypeptide-coated culture surface; wherein the polypeptide is selected from the group consisting of SEQ ID NO: 15 to 24 and 25; and
   (b) culturing pluripotent stem cells on the polypeptide-coated culture surface in culture medium containing 2-mercaptoethanol at a concentration that is equal to or less than 10 μM.

2. The culture method for pluripotent stem cells according to claim 1,
   wherein the concentration of 2-mercaptoethano is equal to or less than 9.0 μM.

3. The culture method for pluripotent stem cells according to claim 1,
   wherein the culture medium does not contain 2-mercaptoethanol.

4. The culture method for pluripotent stem cells according to claim 1,
   wherein the culture medium contains water, a salt, an amino acid, vitamin, selenium, a carbon source, FGF, TGF-β, insulin, and transferrin.

5. The culture method for pluripotent stem cells according to claim 1,
   wherein the culture medium is a serum-free medium.

6. The culture method for pluripotent stem cells according to claim 1,
   wherein a GRAVY value of the polypeptide is −2.0 to −0.95.

7. The culture method for pluripotent stem cells according to claim 1,
   wherein the GRAVY value of the polypeptide is −1.7 to −0.975.

8. The culture method for pluripotent stem cells according to claim 1,
   wherein the support is made of polystyrene having a plasma-treated cell culture surface.

9. The culture method for pluripotent stem cells according to claim 1,
   wherein the pluripotent stem cells are at least one kind of cells selected from the group consisting of embryonic stem cells, induced pluripotent stem cells, somatic stem cells, cells from inner cell mass of fertilized eggs, and early embryonic cells.

10. The culture method for pluripotent stem cells according to claim 1,
wherein the pluripotent stem cells are induced pluripotent stem cells.

11. The culture method for pluripotent stem cells according to claim 1,
wherein the amount of the polypeptide applied to the cell culture surface is 1 pmol/cm$^2$ to 1,000 pmol/cm$^2$.

* * * * *

```
                        SEQUENCE LISTING

<160> NUMBER OF SEQ ID NOS: 39

<210> SEQ ID NO 1
<211> LENGTH: 7
<212> TYPE: PRT
<213> ORGANISM: Artificial Sequence
<220> FEATURE:
<223> OTHER INFORMATION: Partial Sequence of Vitronectin-derived
      Recombinant Protein

<400> SEQUENCE: 1

Cys Ser Tyr Tyr Gln Ser Cys
1               5

<210> SEQ ID NO 2
<211> LENGTH: 32
<212> TYPE: PRT
<213> ORGANISM: Artificial Sequence
<220> FEATURE:
<223> OTHER INFORMATION: Heparin Binding Domain

<400> SEQUENCE: 2

Pro Arg Pro Ser Leu Ala Lys Lys Gln Arg Phe Arg His Arg Asn Arg
1               5                   10                  15

Lys Gly Tyr Arg Ser Gln Arg Gly His Ser Arg Gly Arg Asn Gln Asn
            20                  25                  30

<210> SEQ ID NO 3
<211> LENGTH: 459
<212> TYPE: PRT
<213> ORGANISM: Homo sapiens

<400> SEQUENCE: 3

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95
```

Leu Lys Pro Glu Glu Ala Pro Ala Pro Glu Val Gly Ala Ser Lys
                100                 105                 110

Pro Glu Gly Ile Asp Ser Arg Pro Glu Thr Leu His Pro Gly Arg Pro
            115                 120                 125

Gln Pro Pro Ala Glu Glu Leu Cys Ser Gly Lys Pro Phe Asp Ala
        130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
        355                 360                 365

Gly Arg Asn Gln Asn Ser Arg Arg Pro Ser Arg Ala Thr Trp Leu Ser
370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
            420                 425                 430

Arg Arg Val Asp Thr Val Asp Pro Pro Tyr Pro Arg Ser Ile Ala Gln
        435                 440                 445

Tyr Trp Leu Gly Cys Pro Ala Pro Gly His Leu
450                 455

<210> SEQ ID NO 4
<211> LENGTH: 246
<212> TYPE: PRT
<213> ORGANISM: Artificial Sequence
<220> FEATURE:
<223> OTHER INFORMATION: Polypeptide used for cell culture

<400> SEQUENCE: 4

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
            35                  40                  45

Phe Thr Met Pro Glu Asp Glu Pro Ser Gln Glu Glu Cys Glu Gly Ser
50                  55                  60

Ser Leu Ser Ala Val Phe Glu His Phe Ala Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
                100                 105                 110

Gln Val Asp Ala Ala Met Ala Gly Arg Ile Tyr Ile Ser Gly Met Ala
                115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp Asp Tyr Arg Met Asp Trp
                180                 185                 190

Leu Val Pro Ala Thr Cys Glu Pro Ile Gln Ser Val Phe Phe Phe Ser
                195                 200                 205

Gly Asp Lys Tyr Tyr Arg Val Asn Leu Arg Thr Arg Arg Val Asp Thr
210                 215                 220

Val Asp Pro Pro Tyr Pro Arg Ser Ile Ala Gln Tyr Trp Leu Gly Cys
225                 230                 235                 240

Pro Ala Pro Gly His Leu
                245

<210> SEQ ID NO 5
<211> LENGTH: 87
<212> TYPE: PRT
<213> ORGANISM: Artificial Sequence
<220> FEATURE:
<223> OTHER INFORMATION: Polypeptide used for cell culture

<400> SEQUENCE: 5

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
            35                  40                  45

Phe Thr Met Pro Glu Asp Glu Pro Arg Pro Ser Leu Ala Lys Lys Gln
50                  55                  60

Arg Phe Arg His Arg Asn Arg Lys Gly Tyr Arg Ser Gln Arg Gly His
65                  70                  75                  80

Ser Arg Gly Arg Asn Gln Asn
                85

<210> SEQ ID NO 6
<211> LENGTH: 107
```

-continued

```
<212> TYPE: PRT
<213> ORGANISM: Artificial Sequence
<220> FEATURE:
<223> OTHER INFORMATION: Polypeptide used for cell culture

<400> SEQUENCE: 6

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Gly Val Pro Gly Gln Val Asp Ala Ala
        50                  55                  60

Met Ala Gly Arg Ile Tyr Ile Ser Gly Met Ala Pro Arg Pro Ser Leu
65                  70                  75                  80

Ala Lys Lys Gln Arg Phe Arg His Arg Asn Arg Lys Gly Tyr Arg Ser
                85                  90                  95

Gln Arg Gly His Ser Arg Gly Arg Asn Gln Asn
            100                 105

<210> SEQ ID NO 7
<211> LENGTH: 117
<212> TYPE: PRT
<213> ORGANISM: Artificial Sequence
<220> FEATURE:
<223> OTHER INFORMATION: Polypeptide used for cell culture

<400> SEQUENCE: 7

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Gln Pro Gln Phe Ile Ser Arg Asp Trp
        50                  55                  60

His Gly Val Pro Gly Gln Val Asp Ala Ala Met Ala Gly Arg Ile Tyr
65                  70                  75                  80

Ile Ser Gly Met Ala Pro Arg Pro Ser Leu Ala Lys Lys Gln Arg Phe
                85                  90                  95

Arg His Arg Asn Arg Lys Gly Tyr Arg Ser Gln Arg Gly His Ser Arg
            100                 105                 110

Gly Arg Asn Gln Asn
        115

<210> SEQ ID NO 8
<211> LENGTH: 127
<212> TYPE: PRT
<213> ORGANISM: Artificial Sequence
<220> FEATURE:
<223> OTHER INFORMATION: Polypeptide used for cell culture

<400> SEQUENCE: 8

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
```

```
                35                  40                  45
Phe Thr Met Pro Glu Asp Glu Phe Trp Gly Arg Thr Ser Ala Gly Thr
 50                  55                  60

Arg Gln Pro Gln Phe Ile Ser Arg Asp Trp His Gly Val Pro Gly Gln
 65                  70                  75                  80

Val Asp Ala Ala Met Ala Gly Arg Ile Tyr Ile Ser Gly Met Ala Pro
                 85                  90                  95

Arg Pro Ser Leu Ala Lys Lys Gln Arg Phe Arg His Arg Asn Arg Lys
                100                 105                 110

Gly Tyr Arg Ser Gln Arg Gly His Ser Arg Gly Arg Asn Gln Asn
                115                 120                 125
```

<210> SEQ ID NO 9
<211> LENGTH: 245
<212> TYPE: PRT
<213> ORGANISM: Artificial Sequence
<220> FEATURE:
<223> OTHER INFORMATION: Polypeptide used for cell culture

<400> SEQUENCE: 9

```
Asp Gln Glu Ser Cys Lys Gly Arg Cys Thr Glu Gly Phe Asn Val Asp
 1               5                  10                  15

Lys Lys Cys Gln Cys Asp Glu Leu Cys Ser Tyr Tyr Gln Ser Cys Cys
                 20                  25                  30

Thr Asp Tyr Thr Ala Glu Cys Lys Pro Gln Val Thr Arg Gly Asp Val
                 35                  40                  45

Phe Thr Met Pro Glu Asp Glu Ser Gln Glu Glu Ser Glu Gly Ser Ser
 50                  55                  60

Leu Ser Ala Val Phe Glu His Phe Ala Met Met Gln Arg Asp Ser Trp
 65                  70                  75                  80

Glu Asp Ile Phe Glu Leu Leu Phe Trp Gly Arg Thr Ser Ala Gly Thr
                 85                  90                  95

Arg Gln Pro Gln Phe Ile Ser Arg Asp Trp His Gly Val Pro Gly Gln
                100                 105                 110

Val Asp Ala Ala Met Ala Gly Arg Ile Tyr Ile Ser Gly Met Ala Pro
                115                 120                 125

Arg Pro Ser Leu Ala Lys Lys Gln Arg Phe Arg His Arg Asn Arg Lys
                130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu Glu
                165                 170                 175

Ser Asn Leu Gly Ala Asn Asn Tyr Asp Asp Tyr Arg Met Asp Trp Leu
                180                 185                 190

Val Pro Ala Thr Ser Glu Pro Ile Gln Ser Val Phe Phe Ser Gly
                195                 200                 205

Asp Lys Tyr Tyr Arg Val Asn Leu Arg Thr Arg Val Asp Thr Val
                210                 215                 220

Asp Pro Pro Tyr Pro Arg Ser Ile Ala Gln Tyr Trp Leu Gly Ser Pro
225                 230                 235                 240

Ala Pro Gly His Leu
                245
```

<210> SEQ ID NO 10
<211> LENGTH: 159
<212> TYPE: PRT

<213> ORGANISM: Artificial Sequence
<220> FEATURE:
<223> OTHER INFORMATION: Polypeptide used for cell culture

<400> SEQUENCE: 10

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn
145                 150                 155
```

<210> SEQ ID NO 11
<211> LENGTH: 165
<212> TYPE: PRT
<213> ORGANISM: Artificial Sequence
<220> FEATURE:
<223> OTHER INFORMATION: Polypeptide used for cell culture

<400> SEQUENCE: 11

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg
                165
```

```
<210> SEQ ID NO 12
<211> LENGTH: 175
<212> TYPE: PRT
<213> ORGANISM: Artificial Sequence
<220> FEATURE:
<223> OTHER INFORMATION: Polypeptide used for cell culture

<400> SEQUENCE: 12

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140

Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Ser Glu
                165                 170                 175

<210> SEQ ID NO 13
<211> LENGTH: 185
<212> TYPE: PRT
<213> ORGANISM: Artificial Sequence
<220> FEATURE:
<223> OTHER INFORMATION: Polypeptide used for cell culture

<400> SEQUENCE: 13

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Ser Gln Glu Glu Ser Glu Gly Ser Ser
    50                  55                  60

Leu Ser Ala Val Phe Glu His Phe Ala Met Met Gln Arg Asp Ser Trp
65                  70                  75                  80

Glu Asp Ile Phe Glu Leu Leu Phe Trp Gly Arg Thr Ser Ala Gly Thr
                85                  90                  95

Arg Gln Pro Gln Phe Ile Ser Arg Asp Trp His Gly Val Pro Gly Gln
            100                 105                 110

Val Asp Ala Ala Met Ala Gly Arg Ile Tyr Ile Ser Gly Met Ala Pro
        115                 120                 125

Arg Pro Ser Leu Ala Lys Lys Gln Arg Phe Arg His Arg Asn Arg Lys
    130                 135                 140
```

```
Gly Tyr Arg Ser Gln Arg Gly His Ser Arg Gly Arg Asn Gln Asn Ser
145                 150                 155                 160

Arg Arg Pro Ser Arg Ala Thr Trp Leu Ser Leu Phe Ser Glu Glu
            165                 170                 175

Ser Asn Leu Gly Ala Asn Asn Tyr Asp
        180                 185

<210> SEQ ID NO 14
<211> LENGTH: 142
<212> TYPE: PRT
<213> ORGANISM: Artificial Sequence
<220> FEATURE:
<223> OTHER INFORMATION: Polypeptide used for cell culture

<400> SEQUENCE: 14

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Ser Gln Glu Glu Ser Glu Gly Ser Glu
    50                  55                  60

Asp Ile Phe Glu Leu Leu Phe Trp Gly Arg Thr Ser Ala Gly Thr Arg
65                  70                  75                  80

Gln Pro Gln Phe Ile Ser Arg Asp Trp His Gly Val Pro Gly Gln Val
                85                  90                  95

Asp Ala Ala Met Ala Gly Arg Ile Tyr Ile Ser Gly Met Ala Pro Arg
            100                 105                 110

Pro Ser Leu Ala Lys Lys Gln Arg Phe Arg His Arg Asn Arg Lys Gly
        115                 120                 125

Tyr Arg Ser Gln Arg Gly His Ser Arg Gly Arg Asn Gln Asn
    130                 135                 140

<210> SEQ ID NO 15
<211> LENGTH: 247
<212> TYPE: PRT
<213> ORGANISM: Artificial Sequence
<220> FEATURE:
<223> OTHER INFORMATION: Vitronectin-derived Recombinant Protein (RCP-1)

<400> SEQUENCE: 15

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Pro Ser Gln Glu Glu Cys Glu Gly
    50                  55                  60

Ser Ser Leu Ser Ala Val Phe Glu His Phe Ala Met Met Gln Arg Asp
65                  70                  75                  80

Ser Trp Glu Asp Ile Phe Glu Leu Leu Phe Trp Gly Arg Thr Ser Ala
                85                  90                  95

Gly Thr Arg Gln Pro Gln Phe Ile Ser Arg Asp Trp His Gly Val Pro
            100                 105                 110

Gly Gln Val Asp Ala Ala Met Ala Gly Arg Ile Tyr Ile Ser Gly Met
```

```
            115                 120                 125
Ala Pro Arg Pro Ser Leu Ala Lys Lys Gln Arg Phe Arg His Arg Asn
            130                 135                 140
Arg Lys Gly Tyr Arg Ser Gln Arg Gly His Ser Arg Gly Arg Asn Gln
145                 150                 155                 160
Asn Ser Arg Arg Pro Ser Arg Ala Thr Trp Leu Ser Leu Phe Ser Ser
                165                 170                 175
Glu Glu Ser Asn Leu Gly Ala Asn Asn Tyr Asp Asp Tyr Arg Met Asp
            180                 185                 190
Trp Leu Val Pro Ala Thr Cys Glu Pro Ile Gln Ser Val Phe Phe Phe
            195                 200                 205
Ser Gly Asp Lys Tyr Tyr Arg Val Asn Leu Arg Thr Arg Arg Val Asp
            210                 215                 220
Thr Val Asp Pro Pro Tyr Pro Arg Ser Ile Ala Gln Tyr Trp Leu Gly
225                 230                 235                 240
Cys Pro Ala Pro Gly His Leu
                245

<210> SEQ ID NO 16
<211> LENGTH: 88
<212> TYPE: PRT
<213> ORGANISM: Artificial Sequence
<220> FEATURE:
<223> OTHER INFORMATION: Vitronectin-derived Recombinant Protein (RCP-2)

<400> SEQUENCE: 16

Met Asp Gln Glu Ser Cys Lys Gly Arg Cys Thr Glu Gly Phe Asn Val
1               5                   10                  15
Asp Lys Lys Cys Gln Cys Asp Glu Leu Cys Ser Tyr Tyr Gln Ser Cys
            20                  25                  30
Cys Thr Asp Tyr Thr Ala Glu Cys Lys Pro Gln Val Thr Arg Gly Asp
        35                  40                  45
Val Phe Thr Met Pro Glu Asp Glu Pro Arg Pro Ser Leu Ala Lys Lys
    50                  55                  60
Gln Arg Phe Arg His Arg Asn Arg Lys Gly Tyr Arg Ser Gln Arg Gly
65                  70                  75                  80
His Ser Arg Gly Arg Asn Gln Asn
                85

<210> SEQ ID NO 17
<211> LENGTH: 108
<212> TYPE: PRT
<213> ORGANISM: Artificial Sequence
<220> FEATURE:
<223> OTHER INFORMATION: Vitronectin-derived Recombinant Protein (RCP-3)

<400> SEQUENCE: 17

Met Asp Gln Glu Ser Cys Lys Gly Arg Cys Thr Glu Gly Phe Asn Val
1               5                   10                  15
Asp Lys Lys Cys Gln Cys Asp Glu Leu Cys Ser Tyr Tyr Gln Ser Cys
            20                  25                  30
Cys Thr Asp Tyr Thr Ala Glu Cys Lys Pro Gln Val Thr Arg Gly Asp
        35                  40                  45
Val Phe Thr Met Pro Glu Asp Glu Gly Val Pro Gly Gln Val Asp Ala
    50                  55                  60
Ala Met Ala Gly Arg Ile Tyr Ile Ser Gly Met Ala Pro Arg Pro Ser
65                  70                  75                  80
```

Leu Ala Lys Lys Gln Arg Phe Arg His Arg Asn Arg Lys Gly Tyr Arg
                85                  90                  95

Ser Gln Arg Gly His Ser Arg Gly Arg Asn Gln Asn
            100                 105

<210> SEQ ID NO 18
<211> LENGTH: 118
<212> TYPE: PRT
<213> ORGANISM: Artificial Sequence
<220> FEATURE:
<223> OTHER INFORMATION: Vitronectin-derived Recombinant Protein (RCP-4)

<400> SEQUENCE: 18

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Pro Gln Phe Ile Ser Arg Asp
    50                  55                  60

Trp His Gly Val Pro Gly Gln Val Asp Ala Ala Met Ala Gly Arg Ile
65                  70                  75                  80

Tyr Ile Ser Gly Met Ala Pro Arg Pro Ser Leu Ala Lys Lys Gln Arg
                85                  90                  95

Phe Arg His Arg Asn Arg Lys Gly Tyr Arg Ser Gln Arg Gly His Ser
            100                 105                 110

Arg Gly Arg Asn Gln Asn
        115

<210> SEQ ID NO 19
<211> LENGTH: 128
<212> TYPE: PRT
<213> ORGANISM: Artificial Sequence
<220> FEATURE:
<223> OTHER INFORMATION: Vitronectin-derived Recombinant Protein (RCP-5)

<400> SEQUENCE: 19

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Phe Trp Gly Arg Thr Ser Ala Gly
    50                  55                  60

Thr Arg Gln Pro Gln Phe Ile Ser Arg Asp Trp His Gly Val Pro Gly
65                  70                  75                  80

Gln Val Asp Ala Ala Met Ala Gly Arg Ile Tyr Ile Ser Gly Met Ala
                85                  90                  95

Pro Arg Pro Ser Leu Ala Lys Lys Gln Arg Phe Arg His Arg Asn Arg
            100                 105                 110

Lys Gly Tyr Arg Ser Gln Arg Gly His Ser Arg Gly Arg Asn Gln Asn
        115                 120                 125

<210> SEQ ID NO 20
<211> LENGTH: 246
<212> TYPE: PRT
<213> ORGANISM: Artificial Sequence -continued

```
<220> FEATURE:
<223> OTHER INFORMATION: Vitronectin-derived Recombinant Protein (RCP-6)

<400> SEQUENCE: 20

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp Asp Tyr Arg Met Asp Trp
            180                 185                 190

Leu Val Pro Ala Thr Ser Glu Pro Ile Gln Ser Val Phe Phe Phe Ser
        195                 200                 205

Gly Asp Lys Tyr Tyr Arg Val Asn Leu Arg Thr Arg Arg Val Asp Thr
210                 215                 220

Val Asp Pro Pro Tyr Pro Arg Ser Ile Ala Gln Tyr Trp Leu Gly Ser
225                 230                 235                 240

Pro Ala Pro Gly His Leu
                245

<210> SEQ ID NO 21
<211> LENGTH: 160
<212> TYPE: PRT
<213> ORGANISM: Artificial Sequence
<220> FEATURE:
<223> OTHER INFORMATION: Vitronectin-derived Recombinant Protein (RCP-7)

<400> SEQUENCE: 21

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
```

```
                85                  90                  95
Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

<210> SEQ ID NO 22
<211> LENGTH: 166
<212> TYPE: PRT
<213> ORGANISM: Artificial Sequence
<220> FEATURE:
<223> OTHER INFORMATION: Vitronectin-derived Recombinant Protein (RCP-8)

<400> SEQUENCE: 22

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60

Ser Leu Ser Ala Val Phe Glu His Phe Ala Met Met Gln Arg Asp Ser
65                  70                  75                  80

Trp Glu Asp Ile Phe Glu Leu Leu Phe Trp Gly Arg Thr Ser Ala Gly
                85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg
                165

<210> SEQ ID NO 23
<211> LENGTH: 176
<212> TYPE: PRT
<213> ORGANISM: Artificial Sequence
<220> FEATURE:
<223> OTHER INFORMATION: Vitronectin-derived Recombinant Protein (RCP-9)

<400> SEQUENCE: 23

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Glu Ser Glu Gly Ser
    50                  55                  60
```

```
Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

<210> SEQ ID NO 24
<211> LENGTH: 186
<212> TYPE: PRT
<213> ORGANISM: Artificial Sequence
<220> FEATURE:
<223> OTHER INFORMATION: Vitronectin-derived Recombinant Protein
      (RCP-10)

<400> SEQUENCE: 24

Met Asp Gln Glu Ser Cys Lys Gly Arg Cys Thr Glu Gly Phe Asn Val
  1               5                  10                  15

Asp Lys Lys Cys Gln Cys Asp Glu Leu Cys Ser Tyr Tyr Gln Ser Cys
                 20                  25                  30

Cys Thr Asp Tyr Thr Ala Glu Cys Lys Pro Gln Val Thr Arg Gly Asp
             35                  40                  45

Val Phe Thr Met Pro Glu Asp Glu Ser Gln Glu Ser Glu Gly Ser
         50                  55                  60

Ser Leu Ser Ala Val Phe Glu His Phe Ala Met Met Gln Arg Asp Ser
 65                  70                  75                  80

Trp Glu Asp Ile Phe Glu Leu Leu Phe Trp Gly Arg Thr Ser Ala Gly
                 85                  90                  95

Thr Arg Gln Pro Gln Phe Ile Ser Arg Asp Trp His Gly Val Pro Gly
            100                 105                 110

Gln Val Asp Ala Ala Met Ala Gly Arg Ile Tyr Ile Ser Gly Met Ala
        115                 120                 125

Pro Arg Pro Ser Leu Ala Lys Lys Gln Arg Phe Arg His Arg Asn Arg
    130                 135                 140

Lys Gly Tyr Arg Ser Gln Arg Gly His Ser Arg Gly Arg Asn Gln Asn
145                 150                 155                 160

Ser Arg Arg Pro Ser Arg Ala Thr Trp Leu Ser Leu Phe Ser Ser Glu
                165                 170                 175

Glu Ser Asn Leu Gly Ala Asn Asn Tyr Asp
            180                 185

<210> SEQ ID NO 25
<211> LENGTH: 143
<212> TYPE: PRT
<213> ORGANISM: Artificial Sequence
<220> FEATURE:
<223> OTHER INFORMATION: Vitronectin-derived Recombinant Protein
      (RCP-11)

<400> SEQUENCE: 25
```

Met Asp Gln Glu Ser Cys Lys Gly Arg Cys Thr Glu Gly Phe Asn Val
1               5                   10                  15

Asp Lys Lys Cys Gln Cys Asp Glu Leu Cys Ser Tyr Tyr Gln Ser Cys
            20                  25                  30

Cys Thr Asp Tyr Thr Ala Glu Cys Lys Pro Gln Val Thr Arg Gly Asp
        35                  40                  45

Val Phe Thr Met Pro Glu Asp Glu Ser Gln Glu Ser Glu Gly Ser
    50                  55                  60

Glu Asp Ile Phe Glu Leu Leu Phe Trp Gly Arg Thr Ser Ala Gly Thr
65                  70                  75                  80

Arg Gln Pro Gln Phe Ile Ser Arg Asp Trp His Gly Val Pro Gly Gln
                85                  90                  95

Val Asp Ala Ala Met Ala Gly Arg Ile Tyr Ile Ser Gly Met Ala Pro
            100                 105                 110

Arg Pro Ser Leu Ala Lys Lys Gln Arg Phe Arg His Arg Asn Arg Lys
            115                 120                 125

Gly Tyr Arg Ser Gln Arg Gly His Ser Arg Gly Arg Asn Gln Asn
130                 135                 140

<210> SEQ ID NO 26
<211> LENGTH: 463
<212> TYPE: PRT
<213> ORGANISM: Artificial Sequence
<220> FEATURE:
<223> OTHER INFORMATION: Vitronectin-derived Recombinant Protein
      (RCP-21)

<400> SEQUENCE: 26

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
                20                  25                  30

Gln Ser Cys Cys Thr Asp Tyr Thr Ala Glu Cys Lys Pro Gln Val Thr
            35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
                85                  90                  95

Gln Thr Pro Val Leu Lys Pro Glu Glu Glu Ala Pro Ala Pro Glu Val
            100                 105                 110

Gly Ala Ser Lys Pro Glu Gly Ile Asp Ser Arg Pro Glu Thr Leu His
            115                 120                 125

Pro Gly Arg Pro Gln Pro Pro Ala Glu Glu Glu Leu Cys Ser Gly Lys
    130                 135                 140

Pro Phe Asp Ala Phe Thr Asp Leu Lys Asn Gly Ser Leu Phe Ala Phe
145                 150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
            195                 200                 205

Gly Ser Gln Tyr Trp Arg Phe Glu Asp Gly Val Leu Asp Pro Asp Tyr
    210                 215                 220

```
Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
            245                 250                 255

Tyr Phe Phe Lys Gly Lys Gln Tyr Trp Glu Tyr Gln Phe Gln His Gln
        260                 265                 270

Pro Ser Gln Glu Glu Cys Glu Gly Ser Ser Leu Ser Ala Val Phe Glu
    275                 280                 285

His Phe Ala Met Met Gln Arg Asp Ser Trp Glu Asp Ile Phe Glu Leu
290                 295                 300

Leu Phe Trp Gly Arg Thr Ser Ala Gly Thr Arg Gln Pro Gln Phe Ile
305                 310                 315                 320

Ser Arg Asp Trp His Gly Val Pro Gly Gln Val Asp Ala Ala Met Ala
                325                 330                 335

Gly Arg Ile Tyr Ile Ser Gly Met Ala Pro Arg Pro Ser Leu Ala Lys
            340                 345                 350

Lys Gln Arg Phe Arg His Arg Asn Arg Lys Gly Tyr Arg Ser Gln Arg
        355                 360                 365

Gly His Ser Arg Gly Arg Asn Gln Asn Ser Arg Arg Pro Ser Arg Ala
370                 375                 380

Thr Trp Leu Ser Leu Phe Ser Ser Glu Glu Ser Asn Leu Gly Ala Asn
385                 390                 395                 400

Asn Tyr Asp Asp Tyr Arg Met Asp Trp Leu Val Pro Ala Thr Cys Glu
                405                 410                 415

Pro Ile Gln Ser Val Phe Phe Ser Gly Asp Lys Tyr Tyr Arg Val
            420                 425                 430

Asn Leu Arg Thr Arg Arg Val Asp Thr Val Asp Pro Pro Tyr Pro Arg
            435                 440                 445

Ser Ile Ala Gln Tyr Trp Leu Gly Cys Pro Ala Pro Gly His Leu
    450                 455                 460

<210> SEQ ID NO 27
<211> LENGTH: 272
<212> TYPE: PRT
<213> ORGANISM: Artificial Sequence
<220> FEATURE:
<223> OTHER INFORMATION: Vitronectin-derived Recombinant Protein
      (RCP-22)

<400> SEQUENCE: 27

Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
        35                  40                  45

Arg Gly Asp Val Phe Thr Met Pro Glu Asp Glu Tyr Thr Val Tyr Asp
    50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
                85                  90                  95

Gln Thr Pro Val Leu Lys Pro Glu Glu Glu Ala Pro Ala Pro Glu Val
            100                 105                 110

Gly Ala Ser Lys Pro Glu Gly Ile Asp Ser Arg Pro Glu Thr Leu His
```

```
                115                 120                 125
Pro Gly Arg Pro Gln Pro Pro Ala Glu Glu Leu Cys Ser Gly Lys
        130                 135                 140

Pro Phe Asp Ala Phe Thr Asp Leu Lys Asn Gly Ser Leu Phe Ala Phe
145                 150                 155                 160

Arg Gly Gln Tyr Cys Tyr Glu Leu Asp Glu Lys Ala Val Arg Pro Gly
                165                 170                 175

Tyr Pro Lys Leu Ile Arg Asp Val Trp Gly Ile Glu Gly Pro Ile Asp
            180                 185                 190

Ala Ala Phe Thr Arg Ile Asn Cys Gln Gly Lys Thr Tyr Leu Phe Lys
                195                 200                 205

Gly Ser Gln Tyr Trp Arg Phe Glu Asp Gly Val Leu Asp Pro Asp Tyr
        210                 215                 220

Pro Arg Asn Ile Ser Asp Gly Phe Asp Gly Ile Pro Asp Asn Val Asp
225                 230                 235                 240

Ala Ala Leu Ala Leu Pro Ala His Ser Tyr Ser Gly Arg Glu Arg Val
                245                 250                 255

Tyr Phe Phe Lys Gly Lys Gln Tyr Trp Glu Tyr Gln Phe Gln His Gln
                260                 265                 270
```

<210> SEQ ID NO 28
<211> LENGTH: 134
<212> TYPE: PRT
<213> ORGANISM: Artificial Sequence
<220> FEATURE:
<223> OTHER INFORMATION: Vitronectin-derived Recombinant Protein
      (RCP-23)

<400> SEQUENCE: 28

```
Gly Pro Leu Gly Asp Gln Glu Ser Cys Lys Gly Arg Cys Thr Glu Gly
1               5                   10                  15

Phe Asn Val Asp Lys Lys Cys Gln Cys Asp Glu Leu Cys Ser Tyr Tyr
                20                  25                  30

Gln Ser Cys Cys Thr Asp Tyr Thr Ala Glu Cys Lys Pro Gln Val Thr
            35                  40                  45

Arg Gly Asp Val Phe Thr Met Pro Glu Asp Glu Tyr Thr Val Tyr Asp
50                  55                  60

Asp Gly Glu Glu Lys Asn Asn Ala Thr Val His Glu Gln Val Gly Gly
65                  70                  75                  80

Pro Ser Leu Thr Ser Asp Leu Gln Ala Gln Ser Lys Gly Asn Pro Glu
                85                  90                  95

Gln Thr Pro Val Leu Lys Pro Glu Glu Glu Ala Pro Ala Pro Glu Val
            100                 105                 110

Gly Ala Ser Lys Pro Glu Gly Ile Asp Ser Arg Pro Glu Thr Leu His
        115                 120                 125

Pro Gly Arg Pro Gln Pro
    130
```

<210> SEQ ID NO 29
<211> LENGTH: 59
<212> TYPE: PRT
<213> ORGANISM: Artificial Sequence
<220> FEATURE:
<223> OTHER INFORMATION: Vitronectin-derived Recombinant Protein
      (RCP-24)

<400> SEQUENCE: 29

Gly Pro Leu Gly Asp Gln Glu Ser Cys Lys Gly Arg Cys Thr Glu Gly

```
1               5                   10                  15
Phe Asn Val Asp Lys Cys Gln Cys Asp Glu Leu Cys Ser Tyr Tyr
            20                  25                  30

Gln Ser Cys Cys Thr Asp Tyr Thr Ala Glu Cys Lys Pro Gln Val Thr
            35                  40                  45

Arg Gly Asp Val Phe Thr Met Pro Glu Asp Glu
            50                  55
```

<210> SEQ ID NO 30
<211> LENGTH: 408
<212> TYPE: PRT
<213> ORGANISM: Artificial Sequence
<220> FEATURE:
<223> OTHER INFORMATION: Vitronectin-derived Recombinant Protein (RCP-25)

<400> SEQUENCE: 30

```
Gly Pro Leu Gly Tyr Thr Val Tyr Asp Asp Gly Glu Glu Lys Asn Asn
1               5                   10                  15

Ala Thr Val His Glu Gln Val Gly Gly Pro Ser Leu Thr Ser Asp Leu
            20                  25                  30

Gln Ala Gln Ser Lys Gly Asn Pro Glu Gln Thr Pro Val Leu Lys Pro
            35                  40                  45

Glu Glu Glu Ala Pro Ala Pro Glu Val Gly Ala Ser Lys Pro Glu Gly
            50                  55                  60

Ile Asp Ser Arg Pro Glu Thr Leu His Pro Gly Arg Pro Gln Pro Pro
65              70                  75                  80

Ala Glu Glu Leu Cys Ser Gly Lys Pro Phe Asp Ala Phe Thr Asp
            85                  90                  95

Leu Lys Asn Gly Ser Leu Phe Ala Phe Arg Gly Gln Tyr Cys Tyr Glu
            100                 105                 110

Leu Asp Glu Lys Ala Val Arg Pro Gly Tyr Pro Lys Leu Ile Arg Asp
            115                 120                 125

Val Trp Gly Ile Glu Gly Pro Ile Asp Ala Ala Phe Thr Arg Ile Asn
            130                 135                 140

Cys Gln Gly Lys Thr Tyr Leu Phe Lys Gly Ser Gln Tyr Trp Arg Phe
145                 150                 155                 160

Glu Asp Gly Val Leu Asp Pro Asp Tyr Pro Arg Asn Ile Ser Asp Gly
            165                 170                 175

Phe Asp Gly Ile Pro Asp Asn Val Asp Ala Ala Leu Ala Leu Pro Ala
            180                 185                 190

His Ser Tyr Ser Gly Arg Glu Arg Val Tyr Phe Phe Lys Gly Lys Gln
            195                 200                 205

Tyr Trp Glu Tyr Gln Phe Gln His Gln Pro Ser Gln Glu Glu Cys Glu
            210                 215                 220

Gly Ser Ser Leu Ser Ala Val Phe Glu His Phe Ala Met Met Gln Arg
225                 230                 235                 240

Asp Ser Trp Glu Asp Ile Phe Glu Leu Leu Phe Trp Gly Arg Thr Ser
            245                 250                 255

Ala Gly Thr Arg Gln Pro Gln Phe Ile Ser Arg Asp Trp His Gly Val
            260                 265                 270

Pro Gly Gln Val Asp Ala Ala Met Ala Gly Arg Ile Tyr Ile Ser Gly
            275                 280                 285

Met Ala Pro Arg Pro Ser Leu Ala Lys Lys Gln Arg Phe Arg His Arg
            290                 295                 300
```

Asn Arg Lys Gly Tyr Arg Ser Gln Arg Gly His Ser Arg Gly Arg Asn
305                 310                 315                 320

Gln Asn Ser Arg Arg Pro Ser Arg Ala Thr Trp Leu Ser Leu Phe Ser
            325                 330                 335

Ser Glu Glu Ser Asn Leu Gly Ala Asn Asn Tyr Asp Asp Tyr Arg Met
            340                 345                 350

Asp Trp Leu Val Pro Ala Thr Cys Glu Pro Ile Gln Ser Val Phe Phe
            355                 360                 365

Phe Ser Gly Asp Lys Tyr Tyr Arg Val Asn Leu Arg Thr Arg Arg Val
        370                 375                 380

Asp Thr Val Asp Pro Pro Tyr Pro Arg Ser Ile Ala Gln Tyr Trp Leu
385                 390                 395                 400

Gly Cys Pro Ala Pro Gly His Leu
                405

<210> SEQ ID NO 31
<211> LENGTH: 195
<212> TYPE: PRT
<213> ORGANISM: Artificial Sequence
<220> FEATURE:
<223> OTHER INFORMATION: Vitronectin-derived Recombinant Protein
      (RCP-26)

<400> SEQUENCE: 31

Gly Pro Leu Gly Pro Ser Gln Glu Glu Cys Glu Gly Ser Ser Leu Ser
1               5                   10                  15

Ala Val Phe Glu His Phe Ala Met Met Gln Arg Asp Ser Trp Glu Asp
            20                  25                  30

Ile Phe Glu Leu Leu Phe Trp Gly Arg Thr Ser Ala Gly Thr Arg Gln
        35                  40                  45

Pro Gln Phe Ile Ser Arg Asp Trp His Gly Val Pro Gly Gln Val Asp
    50                  55                  60

Ala Ala Met Ala Gly Arg Ile Tyr Ile Ser Gly Met Ala Pro Arg Pro
65                  70                  75                  80

Ser Leu Ala Lys Lys Gln Arg Phe Arg His Arg Asn Arg Lys Gly Tyr
                85                  90                  95

Arg Ser Gln Arg Gly His Ser Arg Gly Arg Asn Gln Asn Ser Arg Arg
            100                 105                 110

Pro Ser Arg Ala Thr Trp Leu Ser Leu Phe Ser Ser Glu Glu Ser Asn
        115                 120                 125

Leu Gly Ala Asn Asn Tyr Asp Asp Tyr Arg Met Asp Trp Leu Val Pro
    130                 135                 140

Ala Thr Cys Glu Pro Ile Gln Ser Val Phe Phe Phe Ser Gly Asp Lys
145                 150                 155                 160

Tyr Tyr Arg Val Asn Leu Arg Thr Arg Arg Val Asp Thr Val Asp Pro
                165                 170                 175

Pro Tyr Pro Arg Ser Ile Ala Gln Tyr Trp Leu Gly Cys Pro Ala Pro
            180                 185                 190

Gly His Leu
        195

<210> SEQ ID NO 32
<211> LENGTH: 20
<212> TYPE: PRT
<213> ORGANISM: Artificial Sequence
<220> FEATURE:
<223> OTHER INFORMATION: Peptide designed for comparative tests
      (Peptide-1)

<400> SEQUENCE: 32

Asp Gln Glu Ser Cys Lys Gly Arg Cys Thr Glu Gly Phe Asn Val Asp
1               5                   10                  15

Lys Lys Cys Gln
            20

<210> SEQ ID NO 33
<211> LENGTH: 20
<212> TYPE: PRT
<213> ORGANISM: Artificial Sequence
<220> FEATURE:
<223> OTHER INFORMATION: Peptide designed for comparative tests
      (Peptide-2)

<400> SEQUENCE: 33

Lys Gly Arg Cys Thr Glu Gly Phe Asn Val Asp Lys Lys Cys Gln Cys
1               5                   10                  15

Asp Glu Leu Cys
            20

<210> SEQ ID NO 34
<211> LENGTH: 20
<212> TYPE: PRT
<213> ORGANISM: Artificial Sequence
<220> FEATURE:
<223> OTHER INFORMATION: Peptide designed for comparative tests
      (Peptide-3)

<400> SEQUENCE: 34

Glu Gly Phe Asn Val Asp Lys Lys Cys Gln Cys Asp Glu Leu Cys Ser
1               5                   10                  15

Tyr Tyr Gln Ser
            20

<210> SEQ ID NO 35
<211> LENGTH: 20
<212> TYPE: PRT
<213> ORGANISM: Artificial Sequence
<220> FEATURE:
<223> OTHER INFORMATION: Peptide designed for comparative tests
      (Peptide-4)

<400> SEQUENCE: 35

Asp Lys Lys Cys Gln Cys Asp Glu Leu Cys Ser Tyr Tyr Gln Ser Cys
1               5                   10                  15

Cys Thr Asp Tyr
            20

<210> SEQ ID NO 36
<211> LENGTH: 20
<212> TYPE: PRT
<213> ORGANISM: Artificial Sequence
<220> FEATURE:
<223> OTHER INFORMATION: Peptide designed for comparative tests
      (Peptide-5)

<400> SEQUENCE: 36

Cys Cys Thr Asp Tyr Thr Ala Glu Cys Lys Pro Gln Val Thr Arg Gly
1               5                   10                  15

Asp Val Phe Thr
            20

<210> SEQ ID NO 37

```
<211> LENGTH: 20
<212> TYPE: PRT
<213> ORGANISM: Artificial Sequence
<220> FEATURE:
<223> OTHER INFORMATION: Peptide designed for comparative tests
      (Peptide-6)

<400> SEQUENCE: 37

Thr Ala Glu Cys Lys Pro Gln Val Thr Arg Gly Asp Val Phe Thr Met
1               5                   10                  15

Pro Glu Asp Glu
            20

<210> SEQ ID NO 38
<211> LENGTH: 20
<212> TYPE: PRT
<213> ORGANISM: Artificial Sequence
<220> FEATURE:
<223> OTHER INFORMATION: Peptide designed for comparative tests
      (Peptide-7)

<400> SEQUENCE: 38

Cys Cys Thr Asp Tyr Thr Ala Glu Cys Lys Pro Gln Val Thr Arg Gly
1               5                   10                  15

Glu Val Phe Thr
            20

<210> SEQ ID NO 39
<211> LENGTH: 20
<212> TYPE: PRT
<213> ORGANISM: Artificial Sequence
<220> FEATURE:
<223> OTHER INFORMATION: Peptide designed for comparative tests
      (Peptide-8)

<400> SEQUENCE: 39

Thr Ala Glu Cys Lys Pro Gln Val Thr Arg Gly Glu Val Phe Thr Met
1               5                   10                  15

Pro Glu Asp Glu
            20
```